(12) United States Patent
Lees et al.

(10) Patent No.: US 7,101,562 B1
(45) Date of Patent: Sep. 5, 2006

(54) CONJUGATE VACCINES FOR THE PREVENTION OF DENTAL CARIES

(75) Inventors: Andrew Lees, Silver Spring, MD (US); Martin A. Taubman, Newton, MA (US); Daniel J. Smith, Natick, MA (US)

(73) Assignees: The Forsyth Institute, Boston, MA (US); Henry M. Jackson Foundation for the Advancement of Military Medicine, Rockville, MD (US)

( * ) Notice: Subject to any disclaimer, the term of this patent is extended or adjusted under 35 U.S.C. 154(b) by 0 days.

(21) Appl. No.: 09/562,328

(22) Filed: May 1, 2000

Related U.S. Application Data

(63) Continuation-in-part of application No. 09/288,965, filed on Apr. 9, 1999, now abandoned.

(60) Provisional application No. 60/081,315, filed on Apr. 10, 1998.

(51) Int. Cl.
*A61K 39/09* (2006.01)
*A61K 39/02* (2006.01)
*A61K 39/385* (2006.01)
*A61K 39/116* (2006.01)
*C07H 1/00* (2006.01)

(52) U.S. Cl. .............................. 424/244.1; 424/197.11; 424/194.1; 424/234.1; 424/203.1; 424/184.1; 424/831; 514/23; 514/54; 514/835; 530/806; 536/123.12

(58) Field of Classification Search ............. 424/244.1, 424/194.1, 193.1, 197.11, 203.1, 234.1, 184.1, 424/831; 514/23, 835, 59, 54; 536/123.12; 530/807
See application file for complete search history.

(56) References Cited

U.S. PATENT DOCUMENTS

| | | | |
|---|---|---|---|
| 4,150,116 A | 4/1979 | Taubman et al. | ............... 424/88 |
| 4,250,262 A | 2/1981 | Taubman et al. | ............ 435/193 |
| 4,438,200 A | 3/1984 | Taubman et al. | ............ 435/193 |
| 4,789,735 A | 12/1988 | Frank et al. | ................. 530/395 |
| 4,894,229 A | 1/1990 | Polson et al. | .................. 424/92 |
| 5,055,455 A | 10/1991 | Pier | ............................. 514/54 |
| 5,126,131 A | 6/1992 | Dintzis et al. | ................ 424/88 |
| 5,370,871 A | 12/1994 | Dintzis et al. | ............. 424/244.1 |
| 5,585,100 A | 12/1996 | Mond et al. | .............. 424/193.1 |
| 5,651,971 A * | 7/1997 | Lees | ........................ 424/194.1 |
| 5,686,070 A | 11/1997 | Doerschuk et al. | ....... 424/145.1 |
| 5,686,075 A | 11/1997 | Taubman et al. | ....... 424/197.11 |
| 5,693,326 A | 12/1997 | Lees | ........................ 424/194.1 |

FOREIGN PATENT DOCUMENTS

WO    WO 91/07979    6/1991

OTHER PUBLICATIONS

Russell et al. Britsh Dental Journal 152: 81-84, 1982.*
Czerkinsky et al. Infect. Immun. 57: 1072-1077, 1989.*
Taubman MA et al. In: 27th Annual Meeting of the International Association for Dental Research, Minneapolis, MN, #692, Mar. 4-8, 1998.*
Hamada et al. Infect. Immun. 14: 203-211, 1976, abstract.*
Kagnoff et al. Ann. N.Y. Acad. Sci. 409: 114-126, 1983.*
Akoi et al., "Cloning of a *Streptococcus mutans* Glucosyltransferase Gene Coding for Insoluble Glucan Synthesis," Infec. Immun. 53:587-94 (1986).
Aoba et al., "Anti-Peptide Antibodies Reactive with Epitopic Domains of Porcine Amelogenins at the C-Terminus," Archs oral Biol., vol. 37, No. 4, pp. 249-255 (1992).
Banas et al., "Sequence Analysis of the Gene for the Glucan-Binding Protein of *Streptococcus mutans* Ingbritt," Infect. Immun. 58:667-73 (1990).
Beuvery, et al., "Preparation and Immunochemical Characterization of Meningococcal Group C Polysaccharide-Tetanus Toxoid Conjugates as a New Generation of Vaccines," *Infection and Immunity*, vol. 40, No. 1, pp. 39-45, Apr. 1983.
Bowen, et al. eds., "Immunologic Aspects of Dental Caries: Selection of Immunogens for a Caries Vaccine and Cross Reactivity of Antisera to Oral Microorganisms with Mammalian Tissues," Information Retreival Inc., pp. 1-222 (1976).
Brunswick et al., "Picogram Quantities of Anti-Ig Antibodies Coupled to Dextran Induce B Cell Proliferation," J. Immunol., 140:3364-72 (1988).
Chia et al., Analysis of a DNA Polymorphic Region in the gtfB and gtfC Genes of *Streptococcus mutans*, Infect. Immun. 61:1563-66 (1993).
Chia et al., "Antigenicity of a Synthetic Peptide from Glucosyltransferases of *Streptococcus mutans* in Humans," Infect. Immun. 65(3):1126-30 (1997).
Chia et al., "Inhibition of Glucosyltransferase Activities of *Streptococcus mutans* by a Monoclonal Antibody to a Subsequence Peptide," Infect. Immun. 61:4689-95 (1993).

(Continued)

Primary Examiner—S. Devi
(74) Attorney, Agent, or Firm—Mintz,Levin,Cohn,Ferris, Glovsky and Popeo, P.C.; Ingrid A. Beattie

(57) ABSTRACT

The present invention provides glucan-based compositions and methods for stimulating an immune response against mutans streptococci components and vaccines and methods for the treatment and prevention of dental caries. In a preferred embodiment, a glucan polymer, preferably WSG, is covalently bound to one or more T cell-dependent antigens to form a conjugate vaccine. The T cell-dependent antigen preferably contains epitopes of one or more mutans streptococcal proteins, such as a glucosyltransferase. Moreover, one or more moieties, including haptens, may be conjugated to the glucan-T cell-dependent composition. In a preferred embodiment, these moieties are peptides which contain immunogenic epitopes corresponding to components of a mutans streptococcus.

18 Claims, 5 Drawing Sheets

OTHER PUBLICATIONS

Childers et al., "Controlled Clinical Study of Nasal Immunization with *Streptococcus mutans* Antigen Alone or Incorporated Into Liposomes," J. Dent Res. 77, A, 691 (1998).

Cox et al., "Salivary Antibody Response and Priming Stimulated by Soluble or Particulate Antigens Injected at a Remote Secretory Site," Molec. Immunol. 19:171-78 (1982).

Cox et al., "Secretory Antibody Response to Local Injection of Soluble or Particulate Antigens in Rats," Molec. Immunol. 17:1105-15 (1980).

Coykendall et al., "Taxonomy of *Streptococcus mutans*," Molecular Microbiology and Immunobiology of *Streptococcus mutans*," Elsevier Science Publishers, pp. 21-28 (1986).

Dertzbaugh et al., "Choler Toxin B-Subunit Gene Fusion: Structural and Functional Analysis of the Chimeric Protein," Infect. Immun. 58:70-79 (1990).

Eto et al., "Inhibitory Effect of a Self-derived Peptide on Glucosyltransferase of *Streptococcus mutans,*" *The Journal of Biological Chemistry*, vol. 274, No. 22, May 28, 1999, pp. 15797-15802.

Dintzis et al., "The Immunogenicity of Soluble Haptenated Polymers is Determined by Molecular Mass and Hapten Valence," J. Immunol. 143:1239-44 (1989).

Dubois et al., "Colorimetric Method for Determination of Sugars and Related Substances," Anal. Chem. 28:350-56 (1956).

Ebersole, J.L., et al., "Adjuvants, Glucosyltransferase and Caries Vaccine," Proceedings Glucosyltransferase, Glucan, Sucrose, and Dental Caries, Sp. Supp. Chemical Senses, pp. 241-248 (1983).

Ebersole et al., "Regulation of SigA Responses; Adjuvants and Epitope Density," *Journal of Dental Research*, vol. 60, 634, Abstract No. 1299, Mar. 1981.

Ellman, "Tissue Sulfhydryl Groups," Archiv. Biochem. Biophys. 82:70-77 (1959).

Ferretti et al., "Sequence Analysis of the Glucosyltransferase A Gene (gtfA) from *Streptococcus mutans* Ingbritt," Infect. Immun. 56:1585-88 (1988).

Funane et al., "An Active-Site Peptide Containing the Second Essential Carboxyl Group of Dextransucrase from *Leuconostoc mesenteroides* by Chemical Modifications," *Biochemistry*, vol. 32, No. 49, Dec. 1993, pp. 13696-13702.

Gregory, "Dental caries vaccines: science and status," Compendium, 15(10):1282-1286 (1994).

Hajisehengallis et al., "Current status of a mucosal vaccine against detal caries," *Oral Microbiology and Immunology*, 14(1):1-20 (1999).

Hajishengallis et al., "Mucosal Immunization with a Bacterial Protein Antigen Genetically Coupled to Cholera Toxin A2/B Subunits," J. Immunol. 154:4322-32 (1995).

Hamada et al., "Biology, Immunology, and Cariogenicity of *Streptococcus mutans*," Microbiol. Rev. 44(2):331-84 (1980).

Hamada, et al., "An Enzyme-Linked Immunosorbent Assay (Elisa) for Quantification of Antibodies To *Streptococcus mutans* Surface Antigens," *Molecular Immunology*, vol. 20, No. 4 pp. 453-464, 1983.

Hanada et al., "Isolation and Characterization of the *Streptococcus mutans* gtfD Gene, Coding for Primer-Dependent Soluble Glucan Synthesis," Infect. Immun. 57:2079-85 (1989).

Koga et al., "Sucrose-dependent Cell Adherence and Cariogenicity of Serotype *c Streptococcus mutans*," J. Gen. Microbiol. 132:2873-83 (1986).

Lees et al., "Enhanced immunogenicity of protein-dextran conjugates: I. Rapid stimulation of enhanced antibody responses to poorly immunogenic molecules," Vaccine, 12:1160-66 (1994).

Lehner et al., "Immunogenicity of Synthetic Peptides Derived from the Sequences of A *Streptococcus mutans* Cell Surface Antigen in Nonhuman Primates," J. Immunol. 143:2699-705 (1989).

Lett et al., "Musocal Immunogenicity of Polysaccharides Conjugated to a Peptide or Multiple-Antigen Peptide Containing T- and B-Cell Epitopes," Infect and Immun. 63(7):2645-51 (1995).

Lett et al., "Immunogenicity of Polysaccharides Conjugated to Peptides Containing T- and B-Cell Epitopes," Infect. and Immun. 62(3):785-92 (1994).

Lockwood et al., "Treatment of refractory Wegener's granulomatosis with humanized monoclonal antibodies," Q.J. Med. 89:903-12 (1996).

Loesche, "Role of *Streptococcus mutans* in Human Dental Decay," Microbiol. Rev. 50:353-80 (1986).

Ma, "The Caries Vaccine: A Growing Prospect," *Dental Update*, vol. 26, No. 9, Nov. 1999, pp. 374-380.

Ma et al., "Specificity of monoclonal antibodies in local passive immunization against *Streptococcus mutans*," Clin. Exp. Immunol. 77:331-37 (1989).

Michalek et al., "Ingestion of *Streptococcus mutans* Induces Secretory Immunoglobulin A and Caries Immunity," Science 192:1238-40 (1996).

Molina et al., "Improved Performances of Spot Multiple Peptide Synthesis," Pept. Res. 9:151-155 (1996).

Mond et al., "T cell-independent antigens type 2," Annual Review of Immunology, 13:655-692 (1995).

Monsigny et al., "Colorimetric Determination of Neutral Sugars by a Resorcinol Sulfuric Acid Micromethod," Anal. Chem., 175:525-30 (1988).

Mooser et al., "Isolation and Sequence of an Active-site Peptide Containing a Catalytic Aspartic Acid from Two *Streptococcus sobrinus* α-Glucosyltransferases," *The Journal of Biological Chemistry*, vol. 266, No. 14, May 15, 1991, pp. 8916-8922.

O. Makela et al., "Immunogenic Properties of α(1-6) Dextran, Its Proten Conjugates, and Conjugates of Its Breakdown Products in Mice," *Scand. J. Immunol.* 19, 541-550, 1984.

Presta, L., "Humanized Monoclonal Antibodies," Annual Reports in Medicinal Chemistry, vol. 29, 317-24 (Bristol, J. ed., Academic Press 1994).

Rang, et al., "Estimation of Growth Rates of *Escherichia coli* BJ4 in Streptomycin-Threated and Previously Germfree Mice by In Situ rRNA Hybridization," *Clinical and Diagnostic Laboratory Immunology*, vol. 6, No. 3, May 1999, pp. 434-436.

Robbins et al., "Polysaccharide-Protein Conjugates: A New Generation of Vaccines," J. Infect. Dis. 161:821-32 (1990).

Russell et al., "Protein Antigens of *Streptococcus mutans*: Purification and Properties of a Double Antigen and Its Protease-Resistant Component," Infect. Immun. 28:486-43 (1980).

Russell et al., Homology of Glucosyltransferase Gene and Protein Sequences from *Streptococcus sobrinus* and *Streptococcus mutans* J. Dental Res., 67(3):543-47 (1988).

Smith et al., "Vaccines Against Dental Caries Infection," New Generation Vaccines, pp. 913-930, Marcel Dekker, Inc. (1997).

Smith et al., "Antibody to Glucosyltransferase Induced by Synthetic Peptides Associated with Catalytic Regions of α-Amylases," *Infection and Immunity*, vol. 67, No. 5, May 1999, pp. 2638-2642.

Smith et al., "Effects of Local Immunization with Glucosyltransferase on Colonization of Hamsters by *Streptococcus mutans*," Infect. Immun. 37:656-61 (1982).

Smith et al., "Effect of Oral Administration of Glucosyltransferase Antigens on Experimental Dental Carries," Infect. Immun. 26:82-89 (1979).

Smith et al., "Oral Immunization of Humans with *Streptococcus sobrinus* Glucosyltransferase," Infect. Immun. 55:2562-69 (1987).

Smith et al., "Antigenicity and Immunogenicity of a Synthetic Peptide Derived from a Glucan-Binding Domain of Mutans Streptococcal Glucosyltransferase," Infect. Immun. 61:2899-05 (1993).

Smith et al., "Preparation of Glucosyltransferase from *Streptococcus mutans* by Elution from Water-Soluble Polysaccharide with a Dissociating Solvent," Infect. Immun. 23:446-52 (1979).

Smith et al., "Experimental Immunization of Rats with a *Streptococcus mutans* 59-Kilodalton Glucan-Binding Protein Protects against Dental Caries," Infect. and Immun. 64(8):3069-73 (1996).

Smith et al., "Immunogenicity and Protective Immunity Induced by Synthetic Peptides Associated with a Catalytic Subdomain of Mutans Group Streptococcal Glucosyltransferase," Infect. Immun. 65:4424-30 (1997).

Smith et al., "Emergence of Immune Competence in Saliva," Crit. Rev. Oral Biol. Med. 4(3/4):335-41 (1993).

Stack et al., "Dental caries in congenitally athymic rats," Oral Microbiol. Immunol. 5:309-14 (1990).

Takada et al., "Inhibition of plaque and caries formation by a glucan produced by *Streptococcus mutans* mutant UAB108," *Infection and Immunology*, 50(3):833-43 (1985).

Takahashi et al., "Immunogenicity and Protective Effect Against Oral Colonization by *Streptococcus mutans* of Synthetic Peptides of a Streptococcal Surface Protein Antigen," J. Immunol. 146:332-36 (1991).

Taubman et al., "Effects of Local Immunization with Glucosyltransferase Fractions from *Streptococcus mutans* on Dental Caries in Rats and Hamsters," J. Immunol. 118:710-20 (1977).

Taubman et al., "Immune properties of glucosyltransferases from *S. sobrinus*," J. Oral. Pathol. 17:466-70 (1988).

Taubman et al., "An Adjuvant Selective for Secretory Immune Responses," *Journal of Dental Research*, vol. 60, 634, Abstract No. 1298, Mar. 1981.

Taubman et al., "Immunization of Rats with Synthetic Peptide Constructs from the Glucan-Binding or Catalytic Region of Mutans Streptococcal Glucosyltransferase Protects against Dental Caries," Infect. Immun. 63:3088-93 (1995).

Taubman et al., Immunogenicity of Glucan Synthesized by Mutans Streptococcal Glucosyltransferase, J. Dent Res. 77, A, 692 (1998).

Toida et al., "Oral Immunization with the Saliva-Binding Region of *Streptococcus mutans* AgI/II Genetically Coupled to the Cholera Toxin B Subunit Elicits T-Helper-Cell Responses in Gut-Associated Lymphoid Tissues," Infect. Immun. 65(3):909-15 (1997).

Ueda et al., "Sequence analysis of the gtfC gene from *Streptococcus mutans* GS-5," Gene, 69:101-109 (1988).

Vidal et al., "*Trinitrophenyl-protein conjugates are more complex than it is currently thought*," J. Immun. Meth. 86:155-56 (1986).

\* cited by examiner

CONJUGATE VACCINES FOR THE PREVENTION OF DENTAL CARIES

CROSS REFERENCE TO RELATED APPLICATION

This application is a continuation-in-part of application Ser. No. 09/288,965, filed Apr. 9, 1999, now abandoned, which is specifically incorporated by reference, and claims domestic priority to the provisional application Ser. No. 60/081,315, filed Apr. 10, 1998.

GOVERNMENT INTEREST

This invention was made with Government support under NIH grant no. DE-04733 awarded by the National Institutes of Health. The U.S. Government has certain rights in the invention.

FIELD OF THE INVENTION

The present invention relates to the methods of increasing the immunogenicity of glucan epitopes and associated components, preferably, by the preparation of conjugate vaccines comprised of glucan polysaccharides and T cell-dependent antigens, preferably derived from cariogenic Streptococci. In a preferred embodiment, the T cell-dependent antigen is a mutans streptococcal glucose binding protein or glucosyltransferase, fragment, peptide, or combination thereof. The immunogenic compositions of the present invention may be useful in the prevention of dental caries.

BACKGROUND

Dental caries, or tooth decay, results from the erosion of mineral in the enamel and underlying dentin layers of the tooth by the lactic acid secreted by a discrete class of streptococcal bacteria. These cariogenic bacteria, collectively called "mutans streptococci" have been genetically classified into at least four distinct species: *Streptococcus mutans, S. rattus, S. cricetus*, and *S. sobrinus*. Of these, *S. mutans*, and, to a lesser extent, *S. sobrinus*, are common human pathogens. The biology and cariogenic potential of these organisms has been reviewed by A. L. Coykendall and K. B. Gustafson, *Taxonomy of Streptococcus mutans, in Molecular Microbiology and Immunobiology of Streptococcus mutans*. (S. Hamada et al. eds., 1986), Elsevier Science Publishers B. V.; Loesche et al., Microbiol. Rev. 50(4): 353–80 (1986); and Hamada and Slade, Microbiol. Rev. 44(2):331–84 (1980) (incorporated herein by reference).

In the initial stage of infection, mutans streptococci attach to the dental pellicle, or outer covering of the tooth, through bacterial adhesion proteins (e.g., AgI/II protein) specific for pellicular carbohydrates. At this stage, the bacteria present merely a potential threat to dental integrity and are easily removed. However, once this toehold is established, vast numbers of bacteria may accumulate on the tooth surface as dental plaque.

Dental plaque is primarily comprised of bacteria bound together with high molecular weight carbohydrate polymers. These branched, $\alpha$-1,3 and $\alpha$-1,6-linked glucose polymers (glucans) are synthesized from sucrose by a family of extracellular glucosyltransferases or GTFs, constitutively secreted by the cariogenic mutans streptococci. The various GTFs each produce a different form of glucan, broadly classified as either water soluble (WSG) or water insoluble (WIG). Together, these glucans form the basic scaffolding for the aggregation of mutans—and other oral streptococci—through interaction with the catalytic GTFs and nonpolymerizing glucan-binding proteins (GBPs).

The resulting accretion of bacteria and extracellular polysaccharides (plaque) concentrates lactic acid secretions on the tooth surface, shielding the acid from the buffering and dispersing effects of saliva. Chronic lactic acid exposure dissolves the hydroxyapatite of the dentin enamel, allowing bacterial access to the underlying dentin, and ultimately, to the soft, highly sensitive pulp.

Because mutans streptococci require a hard surface for attachment and plaque formation, these bacteria do not thrive in the predentate mouth. Rather, the neonatal oral cavity contains other maternally-derived bacterial flora, primarily the non-cariogenic *Streptococcus salivarius* and *Streptococcus mitis*, which colonize soft epithelial surfaces. Interestingly, the eruption of primary teeth does not result in the immediate colonization of cariogenic streptococci. Rather, and for reasons that are not entirely understood, newly erupted dental surfaces do not usually support the attachment of mutans, but are often colonized by noncariogenic *S. sanguis*. Subsequently, however, oral colonization with mutans streptococci occurs between about eighteen and thirty-six months of age. Although this "window of infectivity" between tooth eruption and mutans colonization remains a poorly understood phenomena, it nevertheless provides a potential opportunity to block mutans invasion before it starts.

Like most infections, mutans streptococcal infections elicit antibody responses in the host, and mounting evidence suggests that a healthy immune system is critical to oral health. Indeed, a low incidence of dental caries has been correlated with high levels of IgG antibodies to mutans surface proteins. Although IgG is usually not considered a secreted protein, antibodies of this isotype may access mutans streptococci at the gumline, through the gingival crevice. Moreover, anti-mutans IgA antibodies, secreted directly into the salivary milieu, appear to block bacterial attachment and plaque formation.

Mutans streptococcal infection is arguably the most common bacterial disease in humans. Moreover, the tooth decay generated by these bacteria represent the principal cause of tooth loss among adults below the age of forty. A properly directed vaccine could reduce the incidence of caries in infected adults. In addition, because children are immunocompetent by this age (Smith and Taubman, Crit. Rev. Oral Biol. Med. 4(3/4):335–41 (1993)), early vaccination could even prevent mutans colonization entirely, potentially resulting in a caries-free mouth.

Thus, the possibility of controlling this caries by active immunization is currently under intensive investigation. The various strategies for creating a prophylactic caries vaccine are reviewed in *Immunologic Aspects of Dental Caries: Selection of Immunogens for a Caries Vaccine and Cross Reactivity of Antisera to Oral Microorganisms with Mammalian Tissues* (W. Bowen, R. Genco & T. O'Brien eds. 1976) Information Retrieval Inc.; and D. J. Smith and M. A. Taubman, *Vaccines Against Dental Caries Infection in New Generation Vaccines* (M. M. Levine, G. C. Woodrow, J. B. Kaper, & G. S. Cobon eds., 2d ed. 1997), Marcel Dekker, Inc., (each of which are incorporated herein by reference). These attempts range from oral ingestion of highly cariogenic strains of whole, killed *S. mutans* bacteria (Michalek et al., Science 192:1238–40 (1996)), to parenteral vaccines using peptides from critical regions of GTF or AgI/II proteins. None of these vaccines has, by themselves, proved to be a panacea against cariogenic infection.

Thus, there remains a need in the art for a safe and efficacious vaccine against mutans streptococci.

SUMMARY OF THE INVENTION

The present invention addresses these needs by providing novel vaccines based on the extracellular glucan component of the cariogenic plaque. Although the glucan may be administered alone, it is preferred that the antigenicity of the glucan be enhanced, preferably, by covalently coupling the glucan to one or more moieties, preferably including at least one T cell-dependent antigen, to form a conjugate vaccine. In a preferred embodiment, the TD antigen contains epitopes of one or more mutans streptococcal proteins, such as AgI/II or a GBP, and preferably, epitopes from a GTF.

In addition, one or more additional moieties, including haptens, may be conjugated to the glucan or to the glucan—TD composition. In a preferred embodiment, these moieties are peptides that contain immunogenic epitopes corresponding to mutans streptococcal components. Preferably, antibodies generated against these epitopes bind to an AgI/II bacterial adhesion protein, or to a GBP, more preferably, to a GTF, and most preferably, to the catalytic or glucan binding site of a GTF.

The present invention thus provides compositions and methods for stimulating an immune response against mutans streptococci components, including glucans and other extracellular or cell associated components, and vaccines and methods for the treatment and prevention of dental caries.

DETAILED DESCRIPTION OF THE INVENTION

Figure 1:
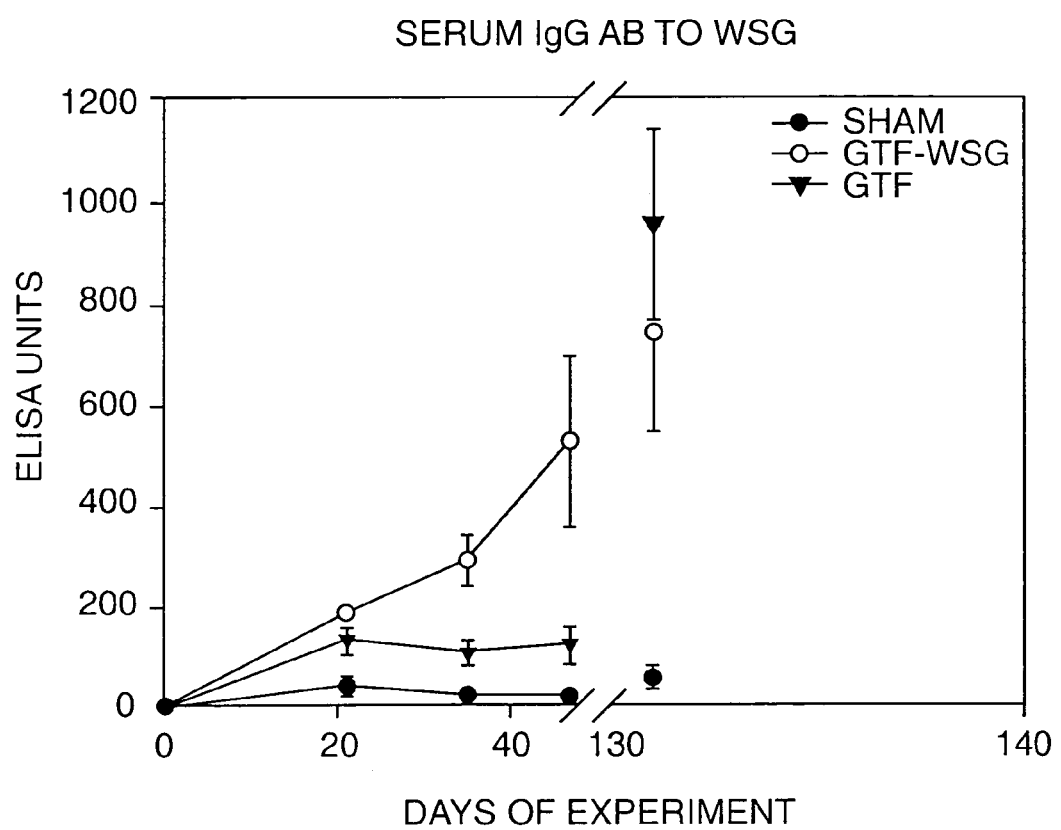
FIG. 1 illustrates level of Serum IgG antibodies induced by vaccination with the GTF-WSG conjugate as compared to GTF alone or PBS (sham) as of 21, 35, 47, and 131 days after the primary inoculation.
Figure 2A:
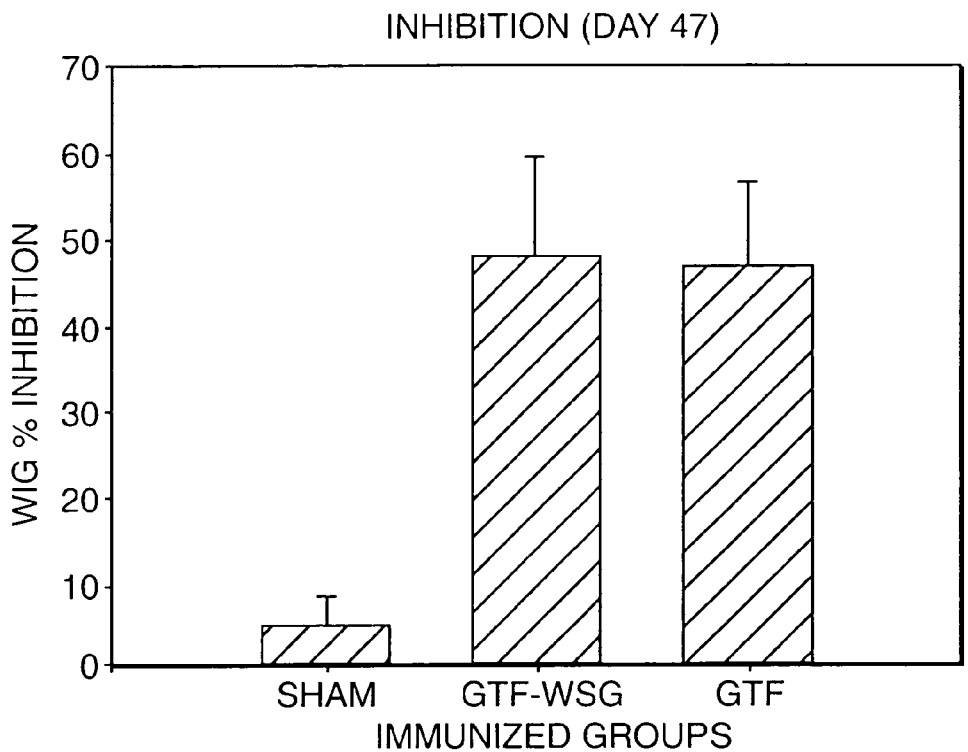
FIGS. 2A and 2B illustrate the percent inhibition of WIG (panel 2A) and WSG (panel 2B) polymerization activity by sera from rats immunized with GTF-WSG versus GTF alone or PBS (sham).
Figure 2B:
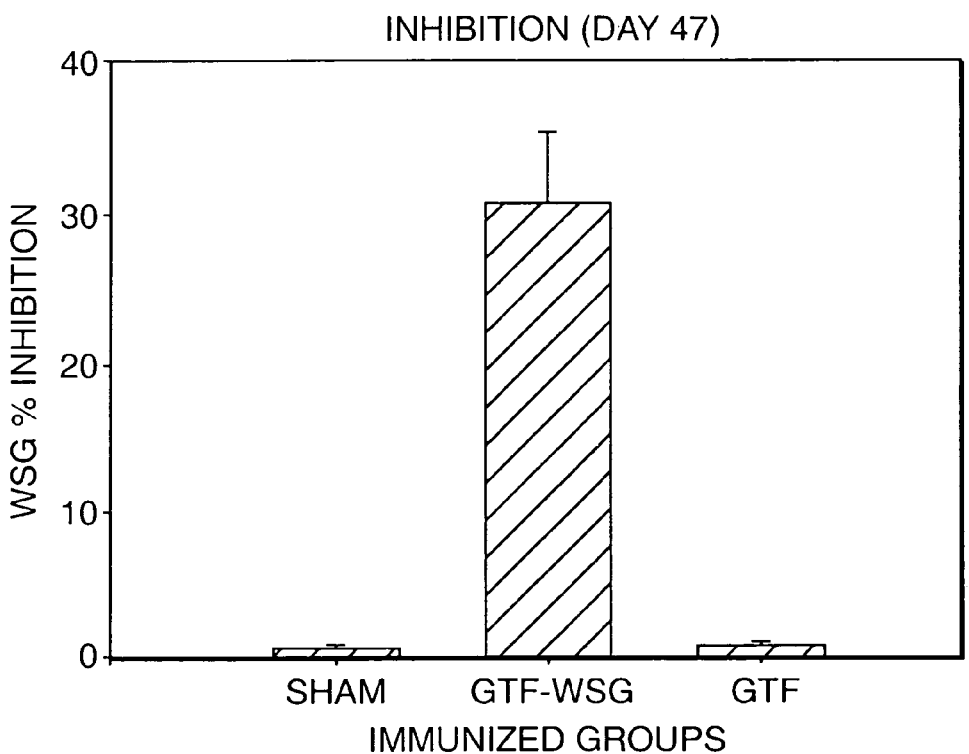

The etiology of dental caries is associated with the acid by-products of bacterial metabolism. The production of these by-products is related to a group of aciduric oral microorganisms collectively referred to as the mutans streptococci. Important microorganisms in this group that are found in humans include *Streptococcus mutans* and *S. sobrinus*. Loesche, Microbiol. Rev. 50: 353–80 (1986).

The infection process and subsequent pathological consequences of mutans colonization occur in a milieu that is perfused with elements of the mucosal and systemic immune systems. In light of this, many immunization strategies have been explored in an attempt to induce immunity to relevant mutans streptococcal virulence components that could ultimately protect the host from dental caries.

Many of these strategies demonstrated a degree of protection in the experimental dental caries caused by infection of a susceptible rat or primate animal model with cariogenic mutans streptococci. Both the active and passive routes have been employed to immunize with mutans streptococci, and isolated mutans components, including those associated with initial attachments ((e.g., adhesin Ag I/II) (Russell et al., Infect. Immun. 28:486–43 (1980); and Ma et al., Clin. Exp. Immunol. 77:331–37 (1989)), or with subsequent accumulation ((e.g., GTF) (Taubman et al., J. Immunol. 118: 710–20 (1977)).

A significant feature of the molecular pathogenesis of dental caries appears to be the role of accumulation of these, and/or related mutans streptococci, in dental plaque. The principle framework of plaque is provided by high molecular weight, branched, glucose polymers called glucans. Glucans are synthesized from sucrose by bacterially secreted glucosyltransferase (GTF) enzymes. Asakawa et al., J. Gen. Microbiol. 132:2873–83 (1988) and Hamada et al., Microbiol. Rev. 44:331–84 (1980).

The glucans of various mutans streptococcal strains contain varying ratios of $\alpha$-1,3 and $\alpha$-1,6 linked glucosidic linkages. Generally, these molecules contain long runs of $\alpha$-1,3 linkages and shorter runs of $\alpha$-1,6 linkages, with frequent branching points in which the same glucosyl residue is bridged to chains of $\alpha$-1,3 and $\alpha$-1,6-linked runs. These molecules are generally classified as water soluble (WSG) and water insoluble glucans (WIG). The degree of water solubility and association of the glucans with the cell surface of the mutans streptococci appears to be a function of the relative predominance of linkage types and of branches. The predominant WSG class is rich in $\alpha$-1,6 linkages, whereas WIG has more $\alpha$-1,3 linkages and is more densely branched. In contrast, dextran, the extracellular polysaccharide of various *Leuconostoc* species, is a virtually pure $\alpha$-1,6 linked linear glucose polymer.

Interference with the synthesis or accumulation of steptoccocal glucans is an opportune target for intervention because the formation of these extracellular polysaccharides is absolutely critical to the cariogenic plaque and resultant caries. Indeed, immunization with GTF, or GTF peptide antigens, may result in protection from experimental dental caries in rodent models, presumably, by preventing the synthesis of extracellular glucans. Taubman et al., J. Immunol. 118:710–20 (1977); Smith et al., Infect. Immun. 37:656–61 (1982); and Smith et al., Infect. Immun. 26:82–89 (1987). In humans, such immunization results in the induction of salivary IgA antibody (SIgA), accompanied by interference with reaccumulation of indigenous mutans streptococci after dental prophylaxis. Smith et al., Infect. Immun. 55:2562–69 (1987). Local injection, gastric intubation, oral administration and topical application have each demonstrated some protective effect using these antigens. Although the exact basis for experimental protection with such GTF-type vaccines is presently unknown, it appears likely that such protection can involve functional inhibition of the catalytic and/or the glucan binding activity of GTF.

Notably, none of these strategies are designed to elicit an antigenic response against the principle structural components of the cariogenic plaque. A single prior study suggested that administration of *S. sobrinus* GTF, which was noncovalently bound to particles of water-insoluble glucan, appeared to elicit a greater secretory immune response than did immunization with soluble GTF. J. L. Ebersole, M. A. Taubman, D. J. Smith, *Adjuvants, Glucosyltransferase and Caries Vaccine*, in Proceedings 'Glucosyltransferase, Glucan, Sucrose, and Dental Caries' (R. Doyle & J. E. Ciardi eds.), Sp. Supp. Chemical Senses, pp. 241–48 (1983). The focus of this study was to elicit antibodies against GTF. Ebersole and coworkers tested GTF combined with Al(OH)$_3$, Freund's and muramyl dipeptide. Along with these known adjuvants, particulate glucan was apparently tested as a depot-type adjuvant, similar to Al(OH)$_3$. Consequently, the presence or absence of an anti-glucan response would have been irrelevant to this study and, indeed, the investigators made no attempt to measure an anti-glucan response.

In contrast to the approaches taken in the prior art, the novel immunogenic compositions and vaccines of the present invention are designed to elicit antibodies against streptococcal glucans themselves. These antibodies provide protection against cariogenic lesions. Although the inventors do not wish to be bound to any particular theory underlying this effect, various scenarios are possible. For example, an immune response to glucan may intercept bacterial aggregation, thereby preventing caries, in several ways. Possibly, anti-glucan antibodies could aggregate and clear mutans streptococci from the oral cavity via cell-bound glucan, or interfere with the binding of glucan to the various non-catalytic glucose binding proteins (GBPs) that contribute to plaque stability. Alternatively, or in addition, anti-glucan antibodies could alter or abrogate the glucan chain lengthening process, by interfering with GTF catalytic activity, or by inhibiting the binding of glucan to GTFs.

The use of glucan as a component of a dental caries vaccine is complicated by the fact that these simple polysaccharides are type 2 T-independent (TI-2) antigens. The TI-2 class of antigens are predominantly linear antigens that are not readily degraded in the body and that have regularly spaced, highly repeating determinants, as reviewed in Mond et al., Ann. Rev. Immun. 14:655–92 (1995). TI-2 antigens commonly comprise large polysaccharide polymers such as those derived from bacterial cell walls or flagella. Other common examples of TI-2 antigens include FICOLL, D-amino acid polymers, polyvinylpyrrolidone, and some highly repetitive polypeptides. When a TI-2 antigen encounters a B cell that expresses cognate cell surface receptors, the antigen binds to multiple B cell surface receptors but is not internalized. A TI-2 antigen generally remains, unprocessed, on the cell surface and stimulates the T-cell independent pathway directly, without direct T cell intervention. Not only do most TI-2 antigen molecules remain intact on the surface of macrophage and B cells, but even if internalized, these antigens are not degraded by endosomal proteases, nor do they efficiently bind to MHC molecules; consequently, they cannot themselves enter the highly productive Class II (T cell-dependent) pathway. Thus, TI-2 antigens induce small primary, and essentially no secondary immune responses. This meager response generally provides little, if any, immunoprotective effect.

Moreover, responses to TI-2 antigens are extremely poor in children less than two years of age. This could suggest against the use of polysaccharide antigens for the twelve to eighteen month old population targeted for a dental caries vaccine. Because children are not generally infected with mutans streptococci prior to about eighteen months of age, vaccination of young children is a particularly preferred method of prophylaxis. Smith & Taubman, Crit. Rev. Oral Biol. Med. 4(3/4):335–41 (1993).

However, conjugating protein or TD peptides to poorly immunogenic TI-2 antigens, significantly improves the induction of immunity to the TI-2 antigen and has resulted in the design of polysaccharide-protein conjugate vaccines now in common use. Robbins and Schneerson, J. Infect. Dis. 161:821–32 (1990); reviewed in *Conjugate Vaccines, in Contrib. Microbiol. Immunol.* Vol. 10, (J. M. Cruse & R. E. Lewis Jr. eds., 1989). For example, diphtheria toxoid has been conjugated to the capsular polysaccharide of *Hemophihus influenzae* (HibDT) and is licensed for administration to children younger than eighteen months old, and Hib vaccinations are recommended as early as 2 months of age. *Physicians' Desk Reference*, pages 1162–1163 (1994); and Recommended Childhood Immunization Schedule United States, for January–June 1996.

Moreover, it has recently been shown that conjugation of a T-dependent antigen to a poorly immunogenic polysaccharide can enhance the immunogenic response to both the T-dependent and T-independent components. In addition, the antibody response to additional moieties, including poorly immunogenic molecules and haptens (including non-TD peptides) can also be dramatically enhanced if further conjugated to the T-dependent or T-independent carrier, or both. Lees et al., Vaccine 1160–66 (1994); U.S. Pat. Nos. 5,585, 100 and 5,955,079 to Mond and Lees, incorporated herein by reference. This enhanced response is particularly pronounced when B cell epitopes of the additional moieties are present in multiple copies.

In one embodiment, antibodies raised against an antigen or hapten bound to the conjugate bind to at least one component of a streptococcal mutans, preferably, a GBP or mutans surface antigen, more preferably, a GTF. In a preferred embodiment a high molecular weight TI-2 antigen, such as a mutans glucan or other high molecular weight bacterial polysaccharide, is covalently bound to at least one TD antigen to form a dual conjugate as defined in Lees et al., Vaccine 1160–66 (1994); and U.S. Pat. Nos. 5,585,100 and 5,955,079 (Mond and Lees).

Moreover, the present invention preferably comprises at least one streptococcal glucan, and at least one T-dependent carrier molecule covalently conjugated to the glucan. As a result of the contributions of both types the TI-2 and TD carriers, the immunogenic constructs of the invention are extremely potent activators of T cell help via mechanisms such as enhanced antigen presentation by B cells, macrophages or other antigen presenting cells. Such a construct can elicit isotype switching, immunological memory, and result in long lived antibody formation against the glucan component in adults and children. The resultant circulating IgG and secretory IgM-class antibodies provide a prophylactic effect against the effects of mutans bacteria.

The glucan component of the invention may be derived from any source, including synthetic, and other bacterial polysaccharides, such as *Leuconostoc* dextrans may also be used. However, it is preferred that the glucans have a structure similar to that synthesized by cariogenic streptococcal mutans, preferably, *S. sobrinus*, most preferably, *S. mutans*. The GTFs of a streptococcal mutan each produce a different form of glucan, broadly classified as WSG (water soluble glucans) or WIG (water insoluble glucans). WSG glucans are preferred. Methods of purifying glucans are well known in the art. Smith et al., Infect. Immun. 61:2899–2905 (1993); Taubman et al., J. Oral. Pathol. 17:466–70 (1988); and Taubman et al., Infect. Immun. 63:3088–93 (1995).

As to the size of the glucans of the invention, it has been suggested that low-molecular weight polysaccharides may inhibit immunogenicity. Dintzis et al., J. Immunol. 143: 1239–44 (1989); Dintzis et al., Fed. Am. Soc. Exp. Biol. 46(3):777 Abstract (1987); Dintzis and Dintzis, Proc. Natl. Acad. Sci. USA 89:1113–17 (1992); Symer et al., J. Immunol. 155:5608–16 (1995); Reim et al., Mol. Immunol. 33:1377–88 (1996); Watson et al., J. Immunol. 156:2443–50 (1996); and Dintzis et al., U.S. Pat. Nos. 5,370,871 and 5,126,131. Moreover, the removal of low molecular weight carbohydrate components may enhance the immunogenicity of the TD components of dual conjugate vaccines. Lees et al., Vaccine 1160–66 (1994); U.S. Pat. Nos. 5,585,100 and 5,955,079 (Mond and Lees). Therefore, the immunogenic compositions of the invention may be purified to remove low molecular weight polysaccharides of less than 100 kDa, 250 kDa, 500 kDa, 750 kDa, 1000 kDa, or 2000 kDa molecular mass. Such purification may be accomplished by HPLC, gel filtration or any other of the number of techniques well known in the art.

The glucan antigen may be administered directly, or bound to a moiety. The moiety may be any molecule other than the glucan, preferably, a TD antigen, or a hapten. However, because TI-2 antigens such as glucan are poorly immunogenic themselves, it is highly preferred that steps be taken to increase the immunogenicity of glucan epitopes.

Thus, in the preferred embodiment, the glucan is associated with, and preferably, covalently bound to at least one TD antigen, forming a dual conjugate composition comprising a TI-2 (glucan) carrier and at least one TD carrier. Additional moieties, including other TD antigens, may be further conjugated to this dual carrier construct.

TD antigens are well known in the art and include, for example, serum albumins, Keyhole Limpet hemocyanin, *E. coli* LT, Horseshoe crab hemocyanin, cholera toxin and toxoid, diphtheria toxoid, pertussis toxoid, tetanus toxoid, and bacterial outermembrane proteins. Some additional TD antigens that may be used in the present invention are described in W. E. Dick and M. Beurret, *Conjugate Vaccines, in Contrib. Microbiol. Immunol.* Vol. 10, pp. 48–114, (J. M. Cruse & R. E. Lewis Jr. eds., 1989), incorporated herein by reference.

In a preferred embodiment, at least one moiety is a TD component derived from a *Streptococcus*, preferably a cariogenic mutans streptococci, preferably, *S. sobrinus*, most preferably, *S. mutans*. A TD antigen is defined as a molecule, generally a protein or peptide, which contains both T and B cell epitopes, and thus elicits a T cell-dependent response. Additional moieties include poorly immunogenic and haptenic molecules, preferably naturally-occurring or synthetic peptides. Haptens are commonly defined as small molecules that are very poorly immunogenic themselves. However, a hapten contains at least one B cell epitope, and thus can be recognized by pre-formed antibodies. In preferred embodiments, the TD antigens and other moieties are either intrinsically multivalent or present in multiple copies.

TD antigens may be identified as containing both T and B cell epitopes according to the procedure of Lett et al., Infect. and Immun 62(3):785–92 (1994), or by any other technique known in the art, including the use of algorithms. Algorithms to predict features associated with T and B epitopes from amino acid sequence data are described in Garnier et al., J. Mol. Biol. 120:97–120 (1978); Hopp et al., Proc. Natl. Acad. Sci. 78 (1981); Rothbard et al., EMBO J. 7:93–100 (1988); and Berzofsky et al., Immunol. Rev. 98:9–52 (1987). Peptides predicted to contain both T and B epitopes can be purified or synthesized and tested for the ability to elicit a T cell-dependent response, for example, by immunizing with the peptide and observing class switching and memory response. Standard techniques for immunization and analysis of the subsequent antibody response are found in *Antibodies: A Laboratory Manual*, (Harlow & Lane eds., 1988), Cold Spring Harbor Laboratory Press, (incorporated herein by reference).

In one embodiment, the TD antigen is an adhesin, or fragment thereof, for example, that described in U.S. Pat. No. 4,789,735 to Frank et al., and the 42 kDa AgII fragment used by Hajishengallis et al., J. Immunol. 154:4322–32 (1995), the disclosures of which are incorporated herein by reference. In a preferred embodiment, the TD component is a GTF, preferably a GTF from a cariogenic streptococcal mutans, more preferably, *S. sobrinus*, and most preferably, *S. mutans*. The term GTF encompasses the naturally occurring, full length amino acid sequence of a glucosyltransferase, as well as any peptide, fusion protein, or fragment thereof containing at least one T- and at least one B-cell dependent epitope. The GTF may be purified from bacteria, produced recombinantly, engineered as a recombinant fusion protein, or synthesized synthetically. Methods for purification of GTF are incorporated herein by U.S. Pat. Nos. 4,250,262 and 4,438,200 (Taubman et al.); and Smith et al., Infect. Immun. 23:446–52 (1979).

The production and expression of recombinant proteins and fusion proteins is well known in the art and can be carried out using conventional procedures, such as those in Sambrook et al. *Molecular Cloning: A Laboratory Manual*, Vols. 1–3, (2d ed. 1989), Cold Spring Harbor Laboratory Press (incorporated herein by reference). GTF or other mutans-specific fusion proteins can also be designed by fusing sequences encoding mutans polypeptides to sequences encoding another polypeptide to aid in the purification of the mutans-specific epitopes. An example of such a fusion is a fusion of sequences encoding a GTF polypeptide to sequences encoding the product of the malE gene of the pMAL-c2 vector of New England Biolabs, Inc., or to a hexahistidine sequence. Such fusions allow for affinity purification of the fusion protein. In addition, methods for removing the non-mutans sequences from the fusion protein after purification are well known in the art. Fusion proteins may also be designed to enhance the immunogenicity of mutans epitopes, for example, by fusing a mutans streptococcal polypeptide sequence to a strong TD antigen such as cholera toxin B subunit. Dertzbaugh et al., Infect. Immun. 58:70–79 (1990).

The moiety may also be a fragment or peptide of a mutans streptococcal protein, preferably, a TD antigen. For example, a GTF may be isolated and purified according to standard methods, and subject to chemical fragmentation. For example, the isolated and purified GTF polypeptide can be treated with cyanogen bromide under conventional conditions that result in fragmentation of the GTF polypeptide by specific hydrolysis on the carboxyl side of the methionine residues within the GTF polypeptide. Gross, Methods in Enz. 11:238–255 (1967). Chemical fragmentation includes the use of cyanogen bromide to cleave under neutral or acidic conditions such that specific cleavage occurs at methionine residues. Gross, Methods in Enz. 11:238–255, (1967). This can further include additional steps, such as a carboxymethylation step to convert cysteine residues to an unreactive species. It is understood of course that many chemicals could be used to fragment mutans polypeptides and that this embodiment in no way limits the scope of the invention.

Alternatively, immunogenic mutans peptides can be generated using enzymes that cleave the polypeptide at specific amino acid residues. For example, an isolated and purified GTF polypeptide can be treated with *Achromobacter* protease I under conventional conditions that result in fragmentation of the GTF polypeptide by specific hydrolysis on the carboxyl side of the lysine residues within the GTF polypeptide. Masaki et al., Biochim. Biophys. Acta 660:44–50 (1981); Masaki et al., Biochim. Biophys. Acta 660:51–55 (1981). Enzymatic fragmentation includes the use of a protease such as Asparaginylendopeptidase, Arginylendopeptidase, *Achrombobacter* protease I, Trypsin, *Staphlococcus aureus* V8 protease, Endoproteinase Asp-N, or Endoproteinase Lys-C under conventional conditions to result in cleavage at specific amino acid residues. Sakiyama and Nakat, U.S. Pat. No. 5,248,599; Masaki et al., Biochim. Biophys. Acta 660:44–50 (1981); Masaki et al., Biochim. Biophys. Acta 660:51–55 (1981); and Cleveland, J. Biol. Chem. 3:1102–06 (1977), which are hereby incorporated by reference. Other enzymatic and chemical treatments can likewise be used to specifically fragment GTF or other streptococcal mutans polypeptides.

Although a part of the invention, naturally-occurring GTF proteins and their derivative peptides are difficult to manufacture in commercial quantities. Consequently, recombinant and synthetically derived materials are preferred. Synthetic GTF polypeptides and peptides can be generated by a variety of conventional techniques using published GTF sequences, e.g., Akoi et al., Infect Immun 53:587–94 (1986); Banas et al., Infect Immun., 58:667–73 (1990); Hanada and Kuramitsu, Infect. Immun 57:2079–85 (1989); Ferretti et al., Infect. Immun. 56:1585–88 (1988); Russell et al., J. Dental Res., 67:543–47 (1988); Ueda et al., Gene, 69:1101–09 (1988), each of which is incorporated by reference. Such techniques include those described in Merrifield, Methods Enzymol. 289:3–13 (1997); Ball and Mascagni, Int. J. Pept. Protein Res. 48:31–47 (1996); Molina et al., Pept. Res. 9:151–155 (1996); Fox, Mol. Biotechnol. 3:249–258 (1995); and Lepage et al., Anal. Biochem. 213: 40–48 (1993), incorporated herein by reference.

In another embodiment, one or more moieties may be directly or indirectly covalently conjugated to the glucan, or to either or both components of the glucan—TD antigen composition. These moieties may be haptens, TI-2 or TD antigens, and are preferably proteins or peptides, most preferably, proteins or peptides from mutans bacteria that have been implicated in cariogenic etiology.

The immunogenic compositions of the invention can employ full length mutans proteins to elicit antibodies which interfere with GTF-mediated glucan synthesis, or otherwise inhibit cariogenic plaque formation. Because full length proteins may contain epitopes which cross-react with host components, or tend to trigger suppressive immune responses that attenuate their effect in some patients, the use of mutans-specific peptides is preferred. The limited epitopes of these peptides elicit protective antibody responses while limiting the immunological risks associated with whole-protein vaccinations.

In a preferred embodiment, the moieties conjugated to the glucan, or to either or both components of the glucan—TD antigen composition are peptides which contain immunogenic epitopes corresponding to components of a mutans streptococci. In one embodiment, antibodies generated against these epitopes bind to an AgI/II bacterial adhesion protein, preferably, to a region implicated in AgI/II binding, for example, the saliva-binding region of Toida et al., Infect Immun. 65(3):909–15 (1997). In another embodiment, antibodies generated against the immunogenic epitopes bind to a glucan binding protein (GBP) (Smith and Taubman, Infect. and Immun. 64(8):3069–73 (1996), incorporated by reference), more preferably, to a GTF, most preferably, to the catalytic or glucan binding site of a GTF. In preferred embodiments, the immunogenic compositions of the invention will elicit antibodies that interfere with the binding properties of a GTF, a glucose binding protein, or an mutans adhesin such as AgI/II. In each case, the interference with binding may be assayed using Scatchard analysis, ELISA analysis, a modification of the techniques described by Eto et. al., J. Biol Chem. 274:15797–802 (1999), Smith et al., Infect Immun. 67:2638–42 (1999), or any number of techniques commonly employed in the art, for example those described in Scatchard et al., Ann. N.Y Acad. Sci., 51:660 (1949); P. Tijssen, *Laboratory Techniques in Biochemistry and Molecular Biology: Practice and Theory of Enzyme Immunoassays*, (Burdon & van Knippenberg eds., 3rd ed., 1985) Elsevier, N.Y.; and *Antibodies: A Laboratory Manual*, (Harlow & Lane eds., 1988), Cold Spring Harbor Laboratory Press, and in U.S. Pat. Nos. 4,376,110 and 4,486,530. (each of which is incorporated by reference).

In a preferred embodiment, at least two, at least three, or at least four different peptides are directly or indirectly conjugated to the glucan carrier. In one embodiment, these peptides are synthesized individually, in tandem arrays of like or unlike sequence, or as components of one or more fusion proteins. In one embodiment, multiple copies of at least one mutans peptide are conjugated to a core matrix, which is then directly, or indirectly, bound to the glucan carrier. Taubman et al., U.S. Pat. No. 5,686,075, incorporated by reference.

Useful peptides will be of sufficient length to raise an immune response when administered to a patient and thus, may be shorter than the complete amino acid sequence of the intact GTF, GBP, adhesin or other mutans protein. Typically a peptide will have at least 5–7, preferably at least 12, and more preferably, at least 18 contiguous amino acids in common with an intact GTF, GPB, or adhesin.

Examples of acceptable peptides are those directed against *S. mutans* surface protein antigen, as described by Takahashi and coworkers (J. Immunol. 146:332–36 (1991)) and the peptide GAVDSILGGVATYGA (SEQ ID NO:1) of Lehner et al., J. Immunol. 143:2699–705 (1989). Preferred peptides are those containing epitopes of an AgI/II protein, including, YEKEPTTPPTRTPDQ (SEQ ID NO:2), TPEDPTDPTDPQDPSS (SEQ ID NO:3), and ANAANEADYQAKLTAYQTEC (SEQ ID NO:4). Lett et al., Infect. and Immun 62(3):785–92 (1994); Lett et al., Infect. and Immun. 63(7):2645–51 (1995); and Takahashi and coworkers (J. Immunol. 146:332–36 (1991), each of which is incorporated by reference.

More preferred peptides are those which contain antigenic epitopes of a GTF. Examples of such peptides have been described by Chia et al., Infect. Immun. 65(3):1126–30, (1997); Smith et al., Infect Immun. 61:2899–905 (1993); Chia et al., Infect. Immun. 61:4689–95 (1993); Lett et al., Infect. Immun. 62:785–92 (1994); Dertzbaugh et al., Infect Immun. 58:70–79 (1990); Chia et al., Infect. Immun. 61:1563–66 (1993); U.S. Pat. Nos. 5,686,070 and 4,150,116 (Taubman et al.); Eto et. al., J. Biol Chem. 274:15797–802 (1999); and Smith et al., Infect Immun. 67:2638–42 (1999), each of which is incorporated herein by reference.

Particularly preferred are peptides from at or near structurally or functionally important regions of a streptococcal adhesin or GTF. Specific examples include peptides from the GTF-derived catalytic aspartate region, peptides described by Mooser et al., J. Biol Chem 266:8916–22 (1991), and those associated with the $\beta_5$, $\beta_7$ or $(\beta,\alpha)_8$ domains of GTF as described by Smith et al., Infect Immun. 67:2638–42 (1999), both of which are incorporated herein by reference. Also particularly preferred are peptides derived from the glucose-binding region of a GTF. In one GTF isolate, the amino acid sequence believed to encode at least part of this function has the sequence TGARTINGQLLYFRANGVQVKG (SEQ ID NO:32), and is a preferred moiety.

Structurally and functionally important peptides can be identified, for example, by observing an effect of peptides or antibodies directed against these peptides on the enzymatic activities of the active protein. Both stimulatory and inhibitory effects indicate the structural or functional importance of the peptidic epitopes. Eto et. al. (J. Biol Chem. 274: 15797–802 (1999)), for example, observed both stimulatory and inhibitory effects on sucrase and GTF-I activity in in vitro assays when adding particular GTF-derived peptides.

Other structurally or functionally important peptides which are particularly useful in the present invention are peptides which contain one or more immunogenic epitopes of GTF comprising amino acids aspartate 413, aspartate 451, histidine 561, aspartate 562, aspartate 567, tryptophan 491, glutamate 489, or arginine 449, which refer to the aspartate residues at amino acid positions 413, 451, 561, 562, 567, 451, 491, 489, and 449, respectively, of S. mutans GTF-B, and described in U.S. patent application Ser. No.: 09/290,049, filed Apr. 12, 1999 issued as U.S. Pat. No. 6,827,936. Similarly within the scope of the invention are immunologic epitopes from corresponding aspartate, histidine, tryptophan, glutamate or arginine residues in other GTFs and GTF variants. As used herein, equivalents of these epitopes residues are intended to include catalytic aspartate and other structurally and functionally important residues present at equivalent sites (positions) in other mutans streptococcal GTFs. That is, the amino acid position numbers of the residues can be different from 413, 451, 561, 562, 567, 451, 491, 489, and 449 in other mutans streptococcal GTFs. These equivalent aspartate residues can be identified, for example, by aligning the amino acid sequences of other streptococcal GTFs based on homology to S. mutans GTF-B. In addition, the characterization of the catalytic properties of an aspartate which is equivalent to aspartate 413, 562, 567 or 451 can be determined by methods described in U.S. patent application Ser. No.: 09/290,049, filed Apr. 12, 1999, issued as U.S. Pat. No. 6,827,936, and Funane et al., Biochem. 32:13696–13702 (1993), both of which are incorporated herein by reference in their entirety.

Similarly, histidine 561, tryptophan 491, glutamate 489 and arginine 449 refer to the histidine, tryptophan, glutamate and arginine residues, respectively, at amino acid positions 561, 491, 489 and 449, respectively, of S. mutans GTF-B. As used herein, equivalents of these histidine, tryptophan, glutamate and arginine residues are intended to include histidine, tryptophan, glutamate and arginine residues, respectively, present at equivalent sites (positions) in other mutans streptococcal GTFs. That is, the amino acid position numbers of these residues can be different in other mutans streptococcal GTFs. These equivalent residues can be identified, for example, by aligning the amino acid sequences of other streptococcal GTFs based on homology to S. mutans GTF-B.

For example, the amino acid sequence can be the amino acid sequence of the EAW peptide ANDHLSILEAWSDNDTPYLHD; (SEQ ID NO:20), the HDS peptide VPSYSFIRTAHDSEVQDLIA (SEQ ID NO:26), or the putative glucan binding peptides TGAQTIKGQKLYFKANGQQVKG (SEQ ID NO:7) and TGARTINGQLLYFRANGVQVKG; (SEQ ID NO:38). The EAW and HDS peptides are particularly immunogenic and antibodies raised against EAW, HDS, or glucan binding peptides have been demonstrated to inhibit the synthesis of WSG in vitro. Smith et al., Infect Immun. 67:2638–42 (1999).

Highly preferred peptides are represented by:

| | |
|---|---|
| DGKLRYYDANSGDQAFNKSV | SEQ ID NO:5; |
| PLDKRSGLNPLIHNSLVDREVDDRE | SEQ ID NO:6; |
| TGAQTIKGQKLYFKANGQQVKG | SEQ ID NO:7; |
| QWNGESEKPYDDHL | SEQ ID NO:8; |
| GGYEFLLANDVDNSNPVVQ | SEQ ID NO:9; |
| ANDVDNSNPVVQAEQLNWL | SEQ ID NO:10; |
| GGYEFLLANDVDNSNPVVQAEQLNWL | SEQ ID NO:11; |
| GGYEDLLANDVDNSNPVVQAEQLNWL | SEQ ID NO:12; |
| GGYEFLLANDVDNSNPIVQAEQLNWL | SEQ ID NO:13; |
| AGYELLLANDVDNSNPVVQAEQLNHL | SEQ ID NO:14; |
| DANFDSIRVDAVDNVDADVVQIA | SEQ ID NO:15; |
| DANFDSIRVDAEDNVDADQLQIS | SEQ ID NO:16; |
| DSIRVDAVD | SEQ ID NO:17; |
| YEKEPTPPTRTPDQ | SEQ ID NO:18; |
| SAWNSDSEKPFDDHL | SEQ ID NO:19; |
| ANDHLSILEAWSDNDTPYLHD | SEQ ID NO:20; |
| ANDHLSILEAWSYNDTPYLHD | SEQ ID NO:21; |
| AINHLSILEAWSDNDPQYNKD | SEQ ID NO:22; |
| ANNHVSIVEAWSDNDTPYLHD | SEQ ID NO:23; |
| AIDHLSILEAWSGNDNDYVKQ | SEQ ID NO:24; |
| ANNHVSIVEAWSDNDTPYLHD | SEQ ID NO:25; |
| VPSYSFIRTAHDSEVQDLIA | SEQ ID NO:26; |
| VPSYSFIRAHDSEVQDLIA | SEQ ID NO:27; |
| VPSYSFIRAHDSEVQDLIRNII | SEQ ID NO:28; |
| MANYIFIRAHDSEVQTVIAKII | SEQ ID NO:29; |
| VPSYSFARAHDSEVQDLIRDII | SEQ ID NO:30; |
| VPNYVFIRAHDSEVQTRIAKII | SEQ ID NO:31; |
| VPSYSFARAHDSEVQDIIRDII | SEQ ID NO:32; |
| PQWNGESEKPYDDHL | SEQ ID NO:33; |
| SAWNSDSEKPFDDHL | SEQ ID NO:34; |
| PNWNSQTESDTSAGE | SEQ ID NO:35; |
| PQWNGESEKPYDDHL | SEQ ID NO:36; |
| TGARTINGQLLYFRANGVQVKG | SEQ ID NO:37; |
| DANFDSIRVDAVDNVDADLLQ | SEQ ID NO:38; |
| DGQVQYFDEMGYQAKGKFV | SEQ ID NO:39; |
| PNKYGTADDLVKAIKALHS | SEQ ID NO:40; |
| LVKAIKALHSKGIKVMADW | SEQ ID NO:41; and |
| VMADWVPDQMYAFPEKEVV | SEQ ID NO:42. |

A peptide within the scope of the invention may be defined in terms of its antigenic relatedness to a GTF or any one or more peptides encoded by SEQ ID NOS:1–42. Thus, in one embodiment, a related peptide within the scope of the invention is defined as an amino acid sequence comprising a linear or 3-dimensional epitope shared with a GTF or any peptide encoded by SEQ ID NOS:1–42. As noted above, methods for predicting antigenic epitopes are known in the art, or such relatedness can be demonstrated empirically by immunizing animals with a polypeptide and testing the resulting antibodies for reactivity against defined subregions of a GTF.

Alternatively, a polypeptide within the scope of the invention is recognized by an antibody which specifically binds to a GTF or any peptide encoded by SEQ ID NOS 1–42. Antibodies are defined to be specifically binding if they bind to a GTF or any one of the peptides of SEQ ID NOS 1–38 with a $K_a$ of greater than or equal to about $10^7$ $M^{-1}$, and preferably greater than or equal to $10^8$ $M^{-1}$.

The invention encompasses both synthetic and naturally-occurring variants of the peptides described in SEQ ID NOS:1–42. Thus, peptides within the scope of the invention comprise both longer and shorter sequences than depicted in SEQ ID NOS:1–42, as well as those which differ in one or more amino acids. Consequently, these variants, are substantially homologous to at least a portion of a native polypeptide, but have an amino acid sequence different from that encoded by any of SEQ ID NOS:1–42 because of one or more deletions, insertions or substitutions. The variant amino acid sequence preferably is at least 80% identical to any of SEQ ID NOS:1–42 or to a native GTF amino acid sequence, preferably at least 85% or 90%, more preferably, at least 95% identical over at least 7, 8, 9, 10, 11, 12, 13, 14, 15, 16, 17, 18, 19, 20, 21–25, or 26–30 contiguous amino acids. The percent identity between an amino acid sequence encoded by any of SEQ ID NOS:1–42 and a potential variant can be determined manually, or, for example, by comparing sequence information using the GAP computer program, version 6.0 descried by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353–358,1979; (2) a penalty of 3.0 for each gap and an additional 0.10 penalty for each symbol in each gap; and (3) no penalty for end gaps.

Variants can comprise conservatively substituted sequences, meaning that a given amino acid residue is replaced by a residue having similar physiochemical characteristics. Examples of conservative substitutions include substitution of one aliphatic residue for another, such as lie, Val, Leu, or Ala for one another, or substitutions of one polar residue for another, such as between Lys and Arg; Glu and Asp; or Gln and Asn. (See Zubay, *Biochemistry*, Addison-Wesley Pub. Co., (1983), incorporated by reference in its entirety.) The effects of such substitutions can be calculated using substitution score matrices such a PAM120, PAM-200, and PAM-250 as discussed in Altshucl, *J. Mol. Biol.* 2.19:555–65 (1991).

In the present invention, moieties, including TD antigens, peptides and haptens, are conjugated to the glucan carrier. This association may be direct, or indirect, for example, through a spacer or linker, a TD antigen, or through any other moiety. Any form of chemical binding, including covalent, is within the scope of this invention. Covalent binding is preferred. Methods of conjugation are well known to those of ordinary skill in the art, and include the hetero-ligation techniques of Brunswick et al., J. Immunol., 140: 3364 (1988); S. S. Wong, *Chemistry of Protein Conjugates and Crosslinking*, (1991), CRC Press, Boston; Brenkeley et al., *Brief Survey of Methods for Preparing Protein Conjugates With Dyes, Haptens and Cross-Linking Agents, in Bioconjugate Chemistry*, 3, No. 1 (January 1992); and G. T. Hermanson, *Bioconjugate Techniques*, (1996), Academic Press, San Diego, each of which are specifically incorporated by reference.

A particularly preferred method of covalent conjugation is via CDAP (1-cyano-4-dimethylamino-pyridinium tetrafluoroborate) activation of the polysaccharide, set forth in application Ser. Nos. 08/482,616 and 08/482,666, filed Jun. 7, 1995, which issued Dec. 15, 1998, as U.S. Pat. No. 5,849, 301, (Ser. No. 08/482,616 being now abandoned), which are a continuation-in-part applications of application Ser. No. 08/408,717, filed Mar. 22, 1995, and issued Jul. 29, 1997, as U.S. Pat. No. 5,651,971, and which is a continuation-in-part of application Ser. No. 08/124,491, filed Sep. 22, 1993, now abandoned, and further set forth in the continuation of application Ser. No. 08/408,717, application Ser. No. 08/456,694, filed Jun. 1, 1995, which issued Dec. 2, 1997 as U.S. Pat. No. 5,693,326, and as further set forth in the continuation-in-part of application Ser. No. 08/124,491, filed Sep. 22, 1993, (now abandoned), the disclosures of which are all specifically incorporated herein by reference. The isourea bond formed by CDAP activation is stable and robust (see, e.g., U.S. Pat. No. 5,651,971, Example 6). The proteins and polysaccharides may be coupled, either directly or indirectly, for example, using a spacer such as one or more amino acids, or the homobifunctional or heterobifunctional vinylsulfones as described in U.S. Provisional Patent Appln. No. 60/017,103 filed on May 9, 1996, and U.S. patent application Ser. No. 08/852,733 filed on May 7, 1997, which issued Oct. 30, 2001, as U.S. Pat. No. 6,309,646, each in the name of Andrew Lees. The protein and/or the polysaccharide can be derivatized or functionalized prior to the conjugation reaction procedure (e.g., with thiols, amines, or hydrazides). Other suitable protein/polysaccharide conjugation techniques for use with this invention include protein/polysaccharide coupling using uronium salts and haloacyl reagents as described in U.S. Pat. No. 6,299,881, issued Oct. 9, 2001, and U.S. Pat. No. 6,087,328, issued Jul. 11, 2000, which claim the benefit of priority of U.S. Provisional Patent Appln. Nos. 60/041,781 (filed Mar. 24, 1997) and 60/042, 379 (filed Apr. 24, 1997), respectively. All of the above-referenced patents and patent applications are entirely incorporated herein by reference.

The process of synthesizing the construct of the invention allows one to advantageously control the physical and chemical properties of the final product. The properties that may be controlled include modifying the charge on primary and secondary carriers (an advantage in light of evidence that cationized proteins may be more immunogenic), varying the size of the construct by varying the size of the TI-2 carriers, selecting the degree of crosslinking of the construct (to obtain variations of size and half-life in the circulation), selecting the number of copies of secondary carriers conjugated to TD carriers, and targeting to selected cell populations (such as to macrophages to enhance antigen presentation).

The immune response to the construct of the invention may be further enhanced by the addition of immunomodulators and/or cell targeting moieties. These entities are co-administered, and preferably chemically conjugated to the immunogenic composition and include, for example, (1) detoxified lipopolysaccharides or derivatives, (2) muramyl dipeptides, (3) carbohydrates, lipids, and peptides that may interact with cell surface determinants to target the construct to immunologically relevant cells, (4) interleukins, such as IL-1, IL-2, IL-4, IL-5, IL-6, IL-10, GM-CSF, or TGF-β and other immunomodulators described, for example in copending application Ser. No. 08/568,343, filed Dec. 6, 1995 (incorporated by reference), and (5) antibodies that may interact with cell surface components. In a preferred embodiment the immunogenicity of the construct may be enhanced by the co-administration or conjugation of an adjuvanting lipoprotein, as described in the copending applications of Mond and Snapper, incorporated herein by reference in their entirety: Induction and Enhancement of the Immune Response to Type 2 T Cell-independent Antigens Conjugated to Lipid or Lipid-containing Moieties, filed Mar. 16, 1998 (Ser. No. 09/039,247) and Induction and Enhancement of the immune response to Polysaccharides with Bacterial Lipoprotein, filed Feb. 5, 1999 (Ser. No. 09/244, 773). Lipoproteins are preferably conjugated to the glucan, TD component, or both, by the methods described in U.S. Pat. No. 5,693,326 to Lees (incorporated herein by reference).

The glucan conjugates of the invention stimulate the immune system to produce anti-mutans antibodies which intercept the GTF-glucan-mediated virulence pathway. Administration of this conjugate to a patient will increase the immunogenicity of the glucan and of any mutans peptide component, resulting in elevated levels of antibody to both peptide and carbohydrate components of the vaccine. The resultant antibody titers will protect against infection with cariogenic mutans streptococci. Although the immunogenic constructs of the invention are broadly applicable to patients in research, clinical, veterinary, and agricultural practice, the degree of protection afforded by a particular construct may be assayed in any of the animal models known in the art, such as the rodent caries model described in Taubman and Smith, J. Immun. 118(2):710–20 (1977) (incorporated herein by reference)

The invention also relates to the treatment of a patient by administration of an immunostimulatory amount of the vaccine. A patient is hereby defined as any person or non-human animal in need of immune stimulation, or to any subject for whom treatment may be beneficial, including humans, and non-human animals. Such non-human animals to be treated include all domesticated and feral vertebrates, preferably but are not limited to mice, rats, rabbits, hamsters, dogs, cats, swine, sheep, horses, cattle, and non-human primates. One of skill in the art will, of course, recognize that the choice of glucan and non-polysaccharide antigens will depend on the streptococcal mutans species or subtypes to be vaccinated against in a particular system. An immunostimulatory amount refers to that amount of vaccine that is able to stimulate the production of antibodies directed against a mutans streptococcal epitope. Preferably, an immunostimulatory amount refers to that amount of vaccine that is able to stimulate an immune response in a patient which is sufficient to prevent, ameliorate, or otherwise treat dental caries.

Secondary booster immunizations may be given at intervals ranging from one week to many months later. The dosage of the primary and secondary inocula can be readily determined by those of ordinary skill in the art, but an acceptable range is 0.01 μg to 100 μg per inoculum. The amount to be administered and the frequency of administration can be determined empirically and will take into consideration the age and size of the patient being treated and the stage of the dental caries disease (e.g., prior to colonization with mutans streptococci, early in the colonization process, or after carious lesions are detected). In a highly preferred embodiment, the patient is vaccinated after the immune system has become competent to respond to the composition, but before the mouth is fully colonized by mutans streptococci. In a human patient, this period spans from about eighteen to 36 months of age. Moreover, treatment may begin as early as two months of age.

Treatment comprises administering the immunogenic composition by any method familiar to those of ordinary skill in the art, including intravenous, intraperitoneal, intracorporeal injection, intra-articular, intraventricular, intrathecal, intramuscular, subcutaneous, topically, tonsillar, intranasally, intravaginally, transcutaneously, and orally. The preferred methods of administration are intravenous, intramuscular, intranasal, oral, and subcutaneous injections. The composition may also be given locally, such as by injection into the particular area, either intramuscularly or subcutaneously.

Administration may be parenteral or local, for example by topical application to the minor salivary glands or injection into the gingiva. In order to increase the amount of mutans-specific IgA antibodies in a patient, it is desirable to promote interaction with gut- or nasal-associated lymphoid tissue (GALT, NALT). Thus, mucosal routes of administration are highly preferred, in particular, oral, gastric, and intranasal administration.

As used herein, a vaccine, or pharmaceutical composition, comprises at least one immunological composition, preferably dissolved or suspended in a pharmaceutically acceptable carrier or vehicle. Any pharmaceutically acceptable carrier can be employed for administration of the composition. Carriers can be sterile liquids, such as water, oils, including petroleum oil, animal oil, vegetable oil, peanut oil, soybean oil, mineral oil, sesame oil, and the like. With intravenous administration, the constructs are preferably water soluble and saline is a preferred carrier. Aqueous dextrose and glycerol solutions can also be employed as liquid carriers, particularly for injectable solutions. Suitable pharmaceutical carriers are described in *Remington's Pharmaceutical Sciences*. 18*th Edition* (A. Gennaro, ed., 1990) Mack Pub., Easton, Pa., incorporated by reference. The immunological composition may also be formulated with solubilizing agents, emulsifiers, stabilizers, flavorants, adjuvants, carriers and other components.

In another embodiment of this invention, antibodies specific for mutans streptococcal glucans can be used to detect the presence of glucans in a sample, or for treatment of a patient by passive immunization, for example, by direct application to the tooth surface. Ma, et al., Clin. Exp. Immunol. 77:331–37 (1989) (incorporated by reference). Monoclonal antibodies are preferred for this application. Any of the compositions of the invention may be used to generate antibodies against mutans streptococci glucans. Thus, the invention encompasses a method of making antibodies comprising administering any of the immunogenic compositions of the invention to a host, and recovering the antibodies. Similarly encompassed is a method of treating a patient against the effects of cariogenic mutans streptococci, comprising administering the antibodies to a patient. In proffered embodiments, the antibodies are monoclonal and humanized.

The term "antibodies" is meant to include polyclonal antibodies, monoclonal antibodies, fragments thereof such as F(ab')2, and Fab fragments. Antibodies are defined to be specifically binding if they inhibit at least one biological activity of a mutans *streptococcus*, for example, the binding of at least one glucan binding proteins (e.g. GTFs and GBPs) to the glucan. Alternatively, an antibody specifically binds if it is displaceable in an ELISA or comparable immunological assay. If the antibody is specific for glucan, for example, antibody binding to glucan can be inhibited by pre-incubation of the antibody with free glucan, as in an ELISA assay. Affinities of antibodies can be readily determined using conventional techniques, for example those described by Scatchard et al., Ann. N.Y Acad. Sci., 51:660 (1949).

Monoclonal antibodies specific for mutans streptococcal glucans can be readily prepared using well-known procedures, see for example, the procedures described in U.S. Pat. No. RE 32,011, U.S. Pat. Nos. 4,902,614, 4,543,439, and 4,411,993; *Monoclonal Antibodies, Hybridomas: A New Dimension in Biological Analyses*, (Kennett, McKearn, & Bechtol eds., 1980), Plenum Press. When used for treating human patients, it is desirable to replace potentially antigenic non-human portions of the antibody with human sequence. A hybrid molecule may be generated in which only the antigen-specific variable, or complementary determining region (CDR) is composed of non-human sequence. These humanized antibodies are thus particularly preferred for clinical use. See, for example, LoBuglio et al., Proc. Natl. Acad. Sci. USA 86:4220–24 (1989); Meredith et al., J. Nucl. Med. 33, 23–29 (1992); Salah et al., Hum. Antibod. Hybridomas 3:19–24 (1992); Knight et al., Mol. Immunol 32:1271–81 (1995); and Lockwood et al., Q.J. Med. 89:903–12, (1996).

Various strategies for designing these humanized antibodies are reviewed in Winter and Milstein, Nature 349:293–99 (1991); Harris, BCSTBS5 23(4):1035–38 (1995); S. Morrison and J. Schlom, *Important Advances in Oncology* (1990), J.B. Lippincott Co.; L. Presta, *Humanized Monoclonal Antibodies, in Annual Resorts in Medicinal Chemistry* (1994) Academic Press; and A. Lewis and J. Crowe, *Generation of Humanized Monoclonal Antibodies by 'Best Fit' Framework Selection and Recombinant Polymerase Chain Reaction", in Generation of Antibodies by Cell and Gene Immortalization*, Year Immunol. Vol. 7, pp. 110–18 (C. Terhorst, F. Malvasi, & A. Albertini eds., 1993), each of which is incorporated herein by reference. As is recognized by one of ordinary skill, corresponding hybrid molecules may be designed for veterinary and agricultural use.

Polyclonal antibodies can be readily generated from a variety of sources, for example, horses, cows, goats, sheep, dogs, chickens, rabbits, mice, or rats, using procedures that are well-known in the art. In general, purified glucan or glucan conjugate is administered to a host animal typically through parenteral injection. The immunogenicity of mutans streptococcal glucans can be enhanced through the use of an adjuvant, for example, Freund's complete or incomplete adjuvant. Following booster immunizations, small samples of serum are collected and tested for reactivity to glucan. Examples of various proceedures and assays useful for the preparation and analysis of polyclonal and monoclonal antibodies are well known in the art and include those described in the series by P. Tijssen, *Laboratory Techniques in Biochemistry and Molecular Biology: Practice and Theory of Enzyme Immunoassays*, (Burdon & van Knippenberg eds., 3rd ed., 1985) Elsevier, N.Y.; and *Antibodies: A Laboratory Manual*, (Harlow & Lane eds., 1988), Cold Spring Harbor Laboratory Press; as well as procedures such as countercurrent immuno-electrophoresis (CIEP), radioimmunoassay, radio-immunoprecipitation, enzyme-linked immuno-sorbent assays (ELISA), dot blot assays, and sandwich assays, see U.S. Pat. Nos. 4,376,110 and 4,486,530, all of which are incorporated by reference.

The present invention is illustrated by the following Examples, which are not intended to be limiting in any way.

EXAMPLE 1

Preparation of Glucan Conjugates

Preparation of GTFs:

GTFs may be purified as described in Smith et al., Infect. Immun., 55:2562–69 (1987); Smith et al., Infect. Immun. 61:2899–2905 (1993); Taubman et al., J. Oral Pathol. 17:466–470 (1988); and Taubman et al., Infect. Immun. 63:3088–93 (1995), incorporated by reference. Briefly, *S. sobrinus* 6715 or *S. mutans* SJ32 are grown in glucose-containing defined media, GTFs, generally comprising GTF-I, GTF-U, and GTF-S, are isolated from culture media by affinity chromatography on SEPHADEX G-100 (Pharmacia), with 3 M guanidine HCl as the eluting solvent. GTF-rich eluate is applied to fast-performance liquid chromatography on SUPEROSE 6 (Pharmacia) with 3 M guanidine HCl for Elution.

WIG and WSG are prepared as follows: *S. mutans*, or *S. sobrinis* 6715 are grown overnight in defined medium containing sucrose, then centrifuged to remove bacterial cells. The cell-free medium containing GTF activities is neutralized with NaOH and dialyzed overnight at 4° C. against PB (20 mM phosphate buffer, pH 6.8, containing 0.2% $NaN_3$). The dialysate is made 3.1% in sucrose and the reaction is incubated for 2 days at 37° C.

WIG is isolated by from the reaction by centrifugation at 10,000×g for 20 min. WSG remains in the supernatent. The pelleted WIG fraction is suspended in PB pH 6.8 and dialyzed overnight against the same buffer at 4° C. Protein contaminants are removed from both the WSG supernatant and the WIG dialysate using the phenol extraction technique. Briefly, the material is extracted with an equal volume of water-saturated phenol.

The WSG fraction is further purified by two, sequential precipitations with 70% ethanol at RT. Following the second ethanol precipitation, the WSG pellet is dissolved in 6 M guanidine HCl and applied to a SEPHAROSE 6, or SEPHAROSE 8, (Pharmacia) gel filtration column run in 6 M guanidine HCl. Effluent fractions are assayed for carbohydrate using the phenol-sulfuric acid technique of Dubois, et al., Anal. Chem. 28:350–56 (1956), incorporated by reference.

The first detectable carbohydrate peak is taken as WSG. The WSG fractions are pooled and dialyzed extensively against PBS.

Analysis of the WIG and WSG fractions using the BCA assay (Pierce Chemical) indicates that the purified glucans are free of detectable protein.

CDAP Conjugation of TD Antigens to Glucan:

Direct conjugation of a polysaccharide and a protein or peptide using CDAP (1-cyano-4-dimethylamino-pyridinium tetrafluoroborate) is essentially as described in Lees, WO 95/08348, incorporated herein by reference. Minor modifications are preferred when the polysaccharide is a glucan and the protein is a glucan-binding protein or @ GTF. As a representative example, WSG is suspended in water @ 10 mg/ml on ice, CDAP @ 100 mg/ml in acetonitrile, 2 mg/ml *S. sobrinus* GTF in physiological saline.

50 μl of CDAP solution is slowly added, with stirring, to 1 ml of glucan solution. At 30 seconds, the pH is raised to approximately 9.5 with about 100 μl of 0.2 M TEA (triethylamine) and maintained at about pH 9.5 with TEA for a total of 2.5 minutes to activate the polysaccharide. After 2.5 minutes, 10 mg of the GTF solution is added to the activated glucan, while mixing. The pH should be in the range of 9–9.5. After 2 hours at RT, the reaction is quenched by the addition of 0.5 ml 2 M glycine @ pH 8 and incubated overnight at RT. The conjugate is then dialyzed against PBS, pooled, and sterile filtered with an 0.2 μm Millipore GV filter. Protein concentration in the dialysate is determined using the BCA assay (Pierce Chemical). The concentration of polysaccharides is determined using the resorcinol/sulfuric acid assay method of Monsigny et al., Anal. Chem., Vol. 175, p. 525 (1988), incorporated herein by reference.

Coupling efficiency using the CDAP procedure is often on the order greater than 70%. Further, when the protein to be coupled tends to bind to the polysaccharide, as with glucan and a GTF, coupling efficiencies will usually exceed 90%. Moreover, unconjugated protein is unlikely to interfere with the antigenicity of the resultant vaccine and may even contribute to the immune response, as suggested by the "Free Protein" application of Lees and Mond (U.S. Ser. No. 09/003,155, filed 06 Jan. 1998, issued as U.S. Pat. No. 6,248,334), incorporated herein by reference. Nevertheless, unconjugated proteins may be removed, for example, by passage over an S500HR (Pharmacia) gel filtration column.

CDAP Conjugation of Peptide Moieties to Glucan, TD Antigens or Glucan-Conjugates:

Peptide moieties may be coupled to the protein, polysaccharide, or protein-polysaccharide conjugate using the following general procedure. A peptide is prepared with an amino-terminal cysteine. The cysteine is reduced in 100 mM DTT and dialyzed extensively against 10 mM sodium acetate, 2 mM EDTA, pH 5 at 4° C. using a dialysis membrane with a molecular weight cutoff of 500. The thiol content of the peptide is determined using Ellman's reagent. (Ellman, Archiv. Biochem. Biophys. 82:70–77 (1959) (Incorporated by reference).

The protein, polysaccharide, or polysaccharide-protein conjugate to be coupled is dialyzed against 150 mM HEPES buffer, 2 mM EDTA, pH 7.3 and labeled in the dark with a 20-fold excess of N-hydroxysuccinimide iodoacetate (SIA) (Pierce Chemical) for 2 hours at RT. Unreacted reagents are then removed by overnight dialysis at 4° C. using dialysis membrane with a molecular weight cutoff of about 10,000.

The reduced peptide and the protein-SIA are degassed under nitrogen and combined at a molar ration of 1 thiolated peptide/mole SIA at pH 7.3. The coupling reaction is allowed to proceed overnight, under nitrogen, in the dark. The reaction is then quenched by addition of Mercaptoethanol to 0.2 mM and unconjugated peptide is removed by ultrafiltration on a membrane with a 50 kDa cutoff and washed into PBS. The peptide and protein content are determined by amino acid analysis and the product is sterile filtered with an 0.2 μm Millipore GV filter.

The conjugates and other reagents used, or to be used, in the following Examples are produced using the general technique described above. Tt-Dex refers to tetanus toxoid conjugated to high molecular weight dextran T2000, (Pharmacia) as described for example, in U.S. Pat. No. 5,585,100, incorporated by reference herein. Tt-WSG and Tt-WIG refer to tetanus toxoid conjugated to water soluble and water insoluble glucan, respectively.

CDAP Conjugation of Tetanus Toxoid to WSG (Tt-WSG)

WSG was suspended in water @ 10 mg/ml on ice, CDAP @ 100 mg/ml in acetonitrile, tetanus toxoid was 16.8 mg/ml in saline (obtained from SmithKline Beecham).

At time zero, 18 μl of CDAP solution was slowly added, with stirring, to 0.25 ml of the WSG glucan solution at RT. At 30 seconds, the pH was raised with 18 μl of 0.2 M TEA (triethylamine). At 60 seconds, an additional 9 μl of TEA was added. At 2.5 minutes, a solution of 150 μl of tetanus toxoid and 25 μl of 100 mM sodium borate, pH 9.3, were added with stirring. The coupling reaction was allowed to proceed for 30 minutes at RT, and then quenched by addition of 100 μl of 1M glycine, pH 9.3. Unconjugated Tt was removed by gel filtration on a 1×60 cm S400HR column (Pharmacia), equilibrated in PBS. The void volume fractions containing the Tt-WSG conjugate were pooled and sterile filtered with an 0.2 μm Millipore GV filter. Protein concentration in the pool was determined using the Coomassie Plus assay (Pierce Chemical). The concentration of polysaccharides was determined using the resorcinol assay of Monsigny et al., Anal. Chem., Vol. 175, p. 525 (1988). The protein/carbohydrate ratio of the Tt-WSG conjugate was 0.7 mgTt/mgWSG.

Tt-mp-WSG was prepared as above except that 160 μl tetanus toxoid (Massachusetts Public Health Laboratories @ 15 mg/ml) and 50 μl of 100 mM sodium borate were used. The protein/carbohydrate ratio of the conjugate was determined to be 1 mg/ml.

CDAP Conjugation of Tetanus Toxoid to WIG (Tt-WIG)

WIG was suspended in saline @ 10 mg/ml on ice, CDAP @ 100 mg/ml in acetonitrile, tetanus toxoid was 16.8 mg/ml in saline (obtained from SmithKline Beecham).

At time zero, 15 μl of CDAP solution was slowly added, with stirring, to 0.23 ml of the WIG glucan solution at RT. At 30 seconds, the pH was raised with 15 μl of 0.2 M TEA (triethylamine). At 2 minutes, 136 μl of tetanus toxoid and 25 μl of 100 mM sodium borate, pH 9.3, were added with stirring. The coupling reaction was allowed to proceed overnight at RT. The reaction mix was then centrifuged to pellet the conjugate. The pellet washed by resuspension in PBS and centrifuged. The pellet was then resuspended in PBS. Protein was determined using the Coomassie Plus assay (Pierce Chemical), and carbohydrate using the resorcinol assay. The protein/carbohydrate ratio of the Tt-WIG conjugate was 0.17 mgTt/mgWIG.

Tt-mp-WIG is similarly prepared using tetanus toxoid obtained from the Massachusetts Public Health Laboratories.

CDAP Conjugation of Tetanus Toxoid to WSG Using a Spacer (Tt-spWSG)

WSG was derivatized with amines using the following procedure. At time zero, 50 μl of CDAP (100 mg/ml in acetonitrile) was added to 1 ml WSG @ 10 mg/ml, with stirring, at RT. At 30 seconds, 50 μl of 0.2 M TEA was added. At 2.5 minutes, 0.5 ml of 0.5 M hexandiamine in sodium borate (pH 9.3) was added and the mixture was stirred for 1 hour at RT. The WSG was desalted on a 1.5×15 cm P6DG column (BioRad), equilibrated with 0.02% $NaN_3$ in saline The product was recovered and concentrated on a FILTRON Macrosep 30 concentrator. The derivatized WSG was determined to have 20.4 amines/100 kDa of glucan using the method of Monsigny et al., Anal. Chem., Vol. 175, p. 525 (1988) to determine carbohydrate and the NTBS method of Vidal and Franci, J. Immum. Meth. 86:155–56 (1986) to determine amines.

250 µl of the aminated WSG (12 mg/ml) was iodoacetylated by stirring with 100 µl of HE buffer (150 mM HEPES, 1 mM EDTA, pH 7.3) and 40 µl of 100 mM N-hydroxysuccinimide iodoacetate (SIA) in dimethylformamide (DMF) for 2 hours at RT in the dark. The reaction was desalted on a 1×15 cm P6DG column (BioRad), equilibrated with 0.02% $NaN_3$ in saline, and concentrated on a FILTRON Macrosep 30.

Tetanus toxoid (179 µl @ 16.8 mg/ml from SmithKline Beecham) was stirred with 100 µl of 0.1M sodium borate, pH 9.3, and thiolated with 9 µl of 25 mM Traut's reagent (Pierce Chemical) in water. The reaction was allowed to proceed for about 2 hours at RT, then desalted on a 1×15 cm P6DG column (BioRad), equilibrated with 0.02% $NaN_3$ in saline. The desalted thiolated tetanus toxoid was concentrated on a FILTRON Macrosep 30.

The thiolated tetanus toxoid was combined with the iodoacetylated WSG in a total volume of 0.75 ml. The pH was raised to 7.5 by addition of 50 µl of HE buffer. The reaction was incubated overnight at 4° C. then quenched by making 0.2 mM mercaptoethanol for 1 hour. Iodoacetamide was then added to a final concentration of about 10 mM.

The conjugate was purified on a 1×60 cm Pharmacia S400HR column, equilibrated in PBS. The void volume fractions containing the Tt-spWSG conjugate were pooled and sterile filtered with an 0.2 µm Millipore GV filter. Protein and polysaccharide concentrations were determined using the Coomassie Plus and resorcinol assays, respectively. The protein/carbohydrate ratio of the Tt-spWSG conjugate was 1.7 mg Tt/mg WSG.

CDAP Conjugation of Tetanus Toxoid to WIG Using a Spacer (Tt-spWIG)

WIG was derivatized with amines using the following procedure. At time zero, 70 µl of CDAP (100 mg/ml in acetonitrile) was added to 920 µl WIG @ 10 mg/ml in saline, with stirring, at RT. At 30 seconds, 70 µl of 0.2 M TEA (triethylamine) was added. At 2.5 minutes, 0.5 ml of 0.5 M hexandiamine in sodium borate (pH 9.3) was added and the mixture was stirred for about 2 hours at RT. The aminated WIG was dialyzed extensively against PBS. The dialysate tested positive for amines using the TNBS assay. Vidal and Franci, J. Immum. Meth. 86:155–56 (1986).

1 ml of the aminated WIG (4 mg/ml) mixed with 100 µl of 5×HE (0.75 M HEPES, 5 mM EDTA, pH 7.3). 100 µl of 100 mM N-hydroxysuccinimide iodoacetate (SIA) in dimethylformamide (DMF) was added and the reaction allowed to proceed for about 2 hours at RT. The product dialyzed overnight against saline to remove the reagent.

238 µl of tetanus toxoid (16.8 mg/ml, SmithKline) was stirred with 50 µl of 0.1M sodium borate, pH 9.3, and thiolated with 2.7 µl of 100 mM Traut's reagent (Pierce Chemical) in water. The reaction was allowed to proceed for about 1 hours at RT, then desalted on a 1×15 cm P6DG column (BioRad), equilibrated with 0.02% $NaN_3$ in saline. The desalted thiolated tetanus toxoid was concentrated on a FILTRON Macrosep 30.

The thiolated tetanus toxoid was combined with the iodoacetylated WIG. The reaction was incubated overnight at 4° C. then quenched by making 0.2 mM mercaptoethanol for 1 hour. The product was pelleted by centrifugation and washed 3–4 times by suspension in 1.5 ml PBS followed by centrifugation. Protein and polysaccharide concentrations were determined using the Coomassie Plus and resorcinol assays, respectively. The protein/carbohydrate ratio of the Tt-spWIG conjugate was 0.33 mgTt/mgWIG.

CDAP Conjugation of Tetanus Toxoid to T2000 Dextran (Tt-Dex)

High molecular weight dextran was prepared by fractionating T2000 Dextran (Pharmacia) on an S400HR column, as described in Lees et al., Vaccine 12:1160–66 (1994). The size-fractionated dextran was suspended in saline @ 10 mg/ml, CDAP @ 100 mg/ml in acetonitrile, tetanus toxoid was 16.8 mg/ml in saline (obtained from SmithKline Beecham).

At time zero, 18 µl of CDAP solution was slowly added, with stirring, to 0.23 ml of the dextran solution at RT. At 30 seconds, the pH was raised with 18 µl of 0.2 M TEA. At 1 minute, an additional 9 µl of 0.2 M TEA was added. At 2.5 minutes, 150 µl of tetanus toxoid and 25 µl of 100 mM sodium borate, pH 9.3, were added with stirring. The coupling reaction was allowed to proceed for 30 minutes at RT then quenched by overnight incubation with 100 µl of 2M glycine, pH 8 at 4° C. Unconjugated Tt was removed by gel filtration on a 1×60 cm S400HR column (Pharmacia), equilibrated in PBS. The void volume fractions containing the Tt-Dex conjugate were pooled and sterile filtered with an 0.2 µm Millipore GV filter. The protein/carbohydrate ratio of the Tt-Dex conjugate was 0.84 mg Tt/mg Dextran T2000.

CDAP Conjugation of GTF to WSG Using a Spacer (GTF-spWSG)

At time zero, 50 µl of CDAP (100 mg/ml in acetonitrile) was added to 1 ml S. mutans WSG @ 10 mg/ml, with stirring, at RT. At 30 seconds, 50 µl of 0.2 M TEA was added. At 2.5 minutes, 0.5 ml of 0.5 M hexandiamine in sodium borate (pH 9.3) was added and the mixture was allowed to proceed overnight. The product was desalted on a 1.5×15 cm P6DG column (BioRad), equilibrated with 0.02% $NaN_3$ in saline The product was then recovered and concentrated on a FILTRON Macrosep 30 microconcentrator concentrator. The derivatized WSG was determined to have 68 amines/100 kDa of glucan.

1 ml of the aminated WSG (4.8 mg/ml) was mixed with 100 µl of 5×HE buffer. 100 µl of 100 mM N-hydroxysuccinimide iodoacetate (SIA) in dimethylformamide (DMF) was added and the reaction allowed to proceed for about 2 hours at RT. The product dialyzed overnight against saline to remove the reagent.

GTF in 6M guanidine HCl (at about 0.5 mg/ml) was dialyzed exhaustively against PBS and concentrated using a FILTRON Macrosep50. Concentration was estimated as 1.7 mg/ml from the area of the UV peak using SEC HPLC. 1.3 ml of the GTF solution was stirred with 200 µl of 0.1 M sodium borate, pH 9.3, and thiolated with 30.6 µl of 10 mM Traut's reagent (Pierce Chemical) in water. The reaction was allowed to proceed for about 2 hours at RT, then dialyzed overnight against PBS to remove the reagents.

The thiolated GTF was combined with the iodoacetylated WIG to a final volume of about 3 ml. The reaction was incubated overnight at 4° C. then quenched by making 0.2 mM mercaptoethanol for 1 hour, then made 10 mM in iodoacetamide. The GTF conjugate was dialyzed against PBS and sterile filtered with an 0.2 µm Millipore GV filter. Protein and polysaccharide concentrations were determined using the Pierce Coomassie Plus and resorcinol assays, respectively. The protein/carbohydrate ratio of the GTF-spWSG conjugate was 0.59 mg GTF/mg WSG.

EXAMPLE 2

Immunogenicity of Streptococcal Mutans Glucans

Groups of 3 Sprague-Dawley rats were immunized with 1 or 10 μg of WIG, or WSG, or PBS, each incorporated in Freund's adjuvant (DIFCO). Animals were inoculated by subcutaneous injection in the vicinity of the the salivary gland and lymph nodes on day 0 in complete adjuvant, and on day 14 in incomplete adjuvant. Serum and saliva samples were extracted on d14 and d29 and tested for IgG and IgA reactivity with *S. sobrinus* glucan.

The Sprague-Dawley rats used herein are derived from germ-free rats that had been reared in the Area 051 isolator facility of Charles River Laboratories and been found to be free of indigenous mutans streptococci. These rats served as the foundation breeding stock for the dams used in these experiments and are regularly monitored for the absence of mutans streptococci. The mutans-free progeny of the dams are weaned at approximately 21 days and are subsequently fed high-sucrose diet 2000. Taubman and Smith, J. Immunol. 118(2):710–20 (1977).

In a separate experiment, groups of 3 Rowett rats (2–3 month old female animals bred at Forsyth Dental Center) were similarly vaccinated, except that serum and saliva samples were extracted on 14, 25, 35, and 42 days after the primary inocculation.

Levels of IgG and IgA in serum samples were examined by ELISA, as described below. An acceptable ELISA assay is also described in *Antibodies: A Laboratory Manual*, (Harlow & Lane eds., 1988), Cold Spring Harbor Laboratory Press (incorporated by reference). Anti-glucan titers were highest after immunization with 10 μg of WSG antigen. Maximal salivary IgA antibody to WSG and WIG was observed 25 days after the primary inoculation. No T-cell proliferative responses against WIG or WSG were observed in cells from glucan-challenged animals.

EXAMPLE 3

Enhanced Immunogenicity of Glucan Conjugate Vaccines

Gnotobiotic Sprague-Dawley rats were immunized subcutaneously in the salivary gland vicinity with PBS, WIG, WSG, Tt, or the Tt conjugates described in Example 1. All polysaccharide inocula were used at doses of 1 or 10 μg (PS Dose). As controls, 1 or 10 μg of tetanus toxoid was injected into Tt animals as controls. Rats were immunized on day 0 with antigen in complete Freund's adjuvant (CFA) and boosted on d14 with the same dose of antigen suspended in incomplete Freund's adjuvant (IFA). Saliva and blood taken from tail veins are collected on d28 and d42 and analyzed for levels of IgG (blood) and IgA (saliva) reactive with WIG, WSG, and Tt.

The compilation of the serum antibody titer data presented in Table I. The results of additional experiments using WSG-GTF conjugates is presented in FIG. 1. In addition, WSG-Tt and WSG-GTF conjugates additionally comprising mutans-derived peptide moieties will be prepared.

T cell Proliferation Assay

Stimulation index (SI) was used to measure the T cell proliferative response induced by the various inoculations. Briefly, T cells were isolated from cervical, brachial, and axillary lymph nodes using standard techniques. The cells were exposed to tritiated thymidine in the presence or absence of Tt, Tt-WSG or Tt-WIG. SI index is the ratio of $^3$H incorporation levels as in the presence/absence of antigen. Each SI index in Table I is mean value from 3 animals. Proliferation assays for each animal are done in triplicate and used to calculate the mean value for the group.

Determination of Antibody Titers:

Antibody titers were determined by a microtiter plate ELISA assay, essentially as described in Stack et al., Oral Microbiol. Immunol. 5:309–14 (1990) and Taubman et al., Infect. and Immun. 63:3088–93 (1995), Cox and Taubman, Molec. Immunol. 19:171–78 (1982); Cox et al., Molec. Immunol. 17:1105–15 (1980); and Engvall and Perlmann, J. Immun. 109:129–35 (1972), incorporated by reference.

The antigens used to coat the wells of 96 well microtiter plates are as follows WSG (10 μg/well), WIG (0.1 μg/well), and Tt (0.1 μg/well). Isotype specific rabbit anti-rat IgA or IgG is used with goat anti-rabbit IgG alkaline phosphatase. (TAGO Inc.) The plates are developed with p-nitrophenyl-phosphate (Sigma) and read on a photometric scanner (Dynatech) at 405 nm. Antibody of each isotype (IgG and IgA) is expressed seperately as ELISA units (EU) of a particular isotype, which are calculated relative to the titration of reference sera from Sprague-Dawley rats hyperimmunized with Tt or with intact mutans streptococci grown in sucrose-containing media. Titrations of reference sera are assayed on each ELISA plate along with titrations of serum or saliva samples. Undiluted reference sera are arbitrarily assigned a value of 100 ELISA units. Sample values are compared to the reference values on each plate to determine the EU value of a sample. It is understood that EU values of different animals, or groups of animals, can be compared with respect to a particular ELISA antigen. However, absolute EU values cannot be directly compared between different ELISA antigens. For example, a sample having an EU of 150 against WSG would have 10 times the amount of anti-WSG activity as a different sample containing 15 EU against the same antigen. However, a sample having 15 EU on a WSG assay, and 150 EU on a WIG assay, does not necessarily contain more or even comparable levels of anti-WIG antibodies.

The results in Table I indicate that covalent binding of Tt to WSG or WIG significantly enhances the anti-glucan serum IgG. Moreover, administration of glucan conjugated to Tt can also enhance the level of anti-glucan IgA antibodies in saliva. There is also a significantly enhanced response to Tt in the conjugates as compared to Tt alone. Indeed, even though the dose of unconjugated Tt in Group 14 is greater than the dose of Tt dose administered as a conjugate in Groups 2, 4, 6, 8, 10, or 12, the antibody responses to Tt are almost invariably higher in the conjugate groups. In addition, the T cell proliferation response to Tt is dramatically higher in animals that received conjugated Tt as compared to animals that received Tt alone. Thus, covalent binding of other TD antigens to the glucan carrier, such as GTF or other mutans proteins, will similarly enhance the antigenicity of the mutans-derived TD antigen and contribute to the prophylactic effect of the vaccine conjugate.

Sera from animals injected with Tt-Dex cross-react with glucan epitopes in the ELISA assay. The basis for this phenomenon is unknown. However, dextran (Dex) is a linear polymer of α1–6 linked glucose, and glucans, especially water soluble glucans, contain stretches of al-6-linked glucose polymer. Consequently, the observed cross-reactivity may reflect antibodies specific for the linear α1–6 portions of the glucan. Thus, the antibodies elicited by the Tt-Dex conjugate may provide a prophylactic effect against mutans infection which has not been previously investigated.

TABLE I

| Group/Ag | PS Dose (μg) | Mean Serum IgG Antibody (EU) vs: | | | Mean Saliva IgA Antibody (EU) vs: | | | Tt | Mean SI vs: | |
|---|---|---|---|---|---|---|---|---|---|---|
| | | WSG | WIG | Tt | WSG | WIG | Tt | | TtWSG | TtWIG |
| 1. Tt-Dex | 1 | 54 | 217 | 10 | | | | | | |
| 2. Tt-Dex | 10 | 31 | 318 | 180 | 90 | 136 | 9 | 4.1 | | |
| 3. Tt-WSG | 1 | 27 | 267 | 20 | | | | | | |
| 4. Tt-WSG | 10 | 266 | 398 | 540 | 90 | 95 | 32 | 8.9 | 9.1 | 6.1 |
| 5. Tt-WIG | 1 | <1 | 6 | <1 | | | | | | |
| 6. Tt-WIG | 10 | 3 | 62 | 100 | 10 | 7 | 3 | 5.2 | | |
| 7. Tt-spWSG | 1 | 15 | 163 | 66 | | | | | | |
| 8. Tt-spWSG | 10 | 38 | 223 | 300 | 35 | 46 | 11 | 2.5 | | |
| 9. Tt-sp-WIG | 1 | 1 | 21 | 20 | | | | | | |
| 10. Tt-sp-WIG | 10 | 2 | 44 | 210 | 10 | 23 | 14 | 2.4 | | |
| 11. Tt-mp-WSG | 1 | 49 | 150 | 20 | | | | | | |
| 12. Tt-mp-WSG | 10 | 79 | 222 | 110 | 113 | 209 | 23 | | | |
| 13. Tt (1 μg) | — | <1 | 10 | <1 | | | | | | |
| 14. Tt (10 μg) | — | <1 | 1 | 110 | 17 | 19 | 7 | 1.8 | 1.8 | 2.8 |
| 15. WSG | 1 | <1 | <1 | <1 | | | | | | |
| 16. WSG | 10 | <1 | 7 | <1 | 50 | 78 | 4 | 0.7 | | |
| 17. WIG | 1 | <1 | <1 | <1 | | | | | | |
| 18. WIG | 10 | <1 | <1 | <1 | 19 | 31 | 5 | 0.7 | | |
| 19. PBS | — | <1 | <1 | <1 | 15 | 6 | 3 | 1.1 | 1.1 | 1.2 |

EXAMPLE 4

Glucan Conjugate Vaccines Inhibit WSG Synthesis

Groups of 7, mutans-free, male Sprague-Dawley rats of approximately 21–23 days of age were injected subcutaneously in the vicinity of the salivary glands (sgv) on d0 with PBS (sham), or with 1 or 10 μg doses of antigen (WSG, GTF, GTF-WSG, Tetanus toxoid (Tt), or Tt-WSG) in complete Freund's antigen, as described above. On d7, and again on d117, each animal was boosted with the same dose of antigen or PBS suspended in incomplete Freund's adjuvant (IFA).

Blood samples taken on days 21, 35, 47, 124, 131, 145, 159 and 175 were analyzed for serum IgG titers to WSG and GTF. As shown in FIG. 1, immunization with the GTF-WSG conjugate results in a marked increase in serum IgG immune response to WSG. In contrast, immunization with GTF alone produces only a marginal increase in anti-WSG titer.

Sera from immunized rats were analyzed for the ability to inhibit GTF-mediated glucan polymerization. Briefly, GTF activity is measured by determining the extent of $^{14}$C-glucose incorporation from gucosyl-labeled sucrose into complex polysaccharides as described in Taubman et al., Infect. Immun. 63:3088–93 (1995) and Taubman and Smith, J. Immunol. 118:710–20, both of which are incorporated by reference. Although inoculation with either GTF or GTF-WSG inhibits the production of WIG from sucrose, WSG synthesis is significantly inhibited only in sera of animals vaccinated with the GTF-WSG conjugate.

On d175, the animals were sacrificed and stimulation indices (SI) determined using the T cell proliferation assay described above. The results of this assay are presented in Table II. T cell proliferation responses were significantly elevated in animals immunized with the GTF and GTF-WSG conjugate.

TABLE II

| Immunized Group | Test Antigens Stimulation Index (mean ± standard error) | | | |
|---|---|---|---|---|
| | WSG | Tt-WSG | GTF-WSG | GTF |
| Tt-WSG | 1 ± 0 | 10 ± 2 | 4 ± 1 | 1 ± 0 |
| Tt | 1 ± 0 | 4 ± 1 | 2 ± 1 | 2 ± 1 |
| GTF-WSG | 1 ± 0 | 1 ± 0 | 19 ± 1 | 15 ± 3 |
| GTF | 1 ± 0 | 1 ± 0 | 20 ± 6 | 17 ± 5 |

EXAMPLE 5

Glucan Conjugate Vaccines Stimulate Production of Salivary Anti-IgA Antibodies Against WSG and GTF Groups of 10–11, mutans-free, male Sprague-Dawley rats of approximately 40 days of age were injected subcutaneously in the vicinity of the salivary glands (sgv) on d0 with PBS (sham), or 10 μg doses of WSG, GTF, GTF-WSG, Tetanus toxoid (Tt), or Tt-WSG, as described above, each suspended in Freund's complete adjuvant. On d7, each animal was boosted with the same dose of antigen or PBS suspended in incomplete Freund's adjuvant (IFA).

Beginning on day 22, rats were orally infected with approximately $10^8$ S. sobrinus 6715 cells for 3 consecutive days. Rats were singly caged after the infection series until terminated at d101.

The presence of mutans streptococcal flora was assessed at 32 days and at termination, as described in Taubman et al., Infect. Immun. 63:3088–93 (1995), incorporated by reference. Briefly, teeth were systematically swabbed and the swabs sonicated. The sonicate was serially diluted and plated onto mitis salivarius (MS) agar (to determine total streptococci), and on MS agar further including 200 μg of streptomycin per ml (MSS agar). Plates were incubated at 37° in 90% $N_2$—10% $CO_2$ for 48 hours, at which time total and mutans streptococci CFU were enumerated microscopically.

All intentionally infected rats exhibited significant titers of the *S. sobrinus* at both time points, indicating successful and stable colonization with the test bacteria. To ascertain that no horizontal transmission occurred, sentinal animals housed in close proximity were tested concurrently. As expected, swabs from these control animals were negative for *S. sobrinus*.

Figure 3A:
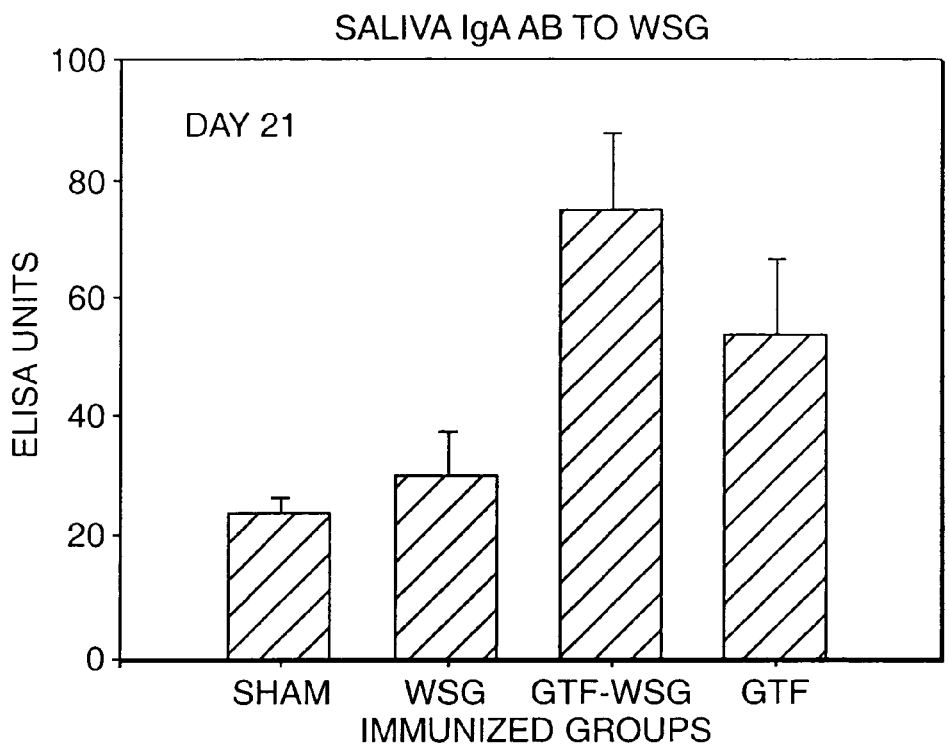
FIGS. 3A and 3B illustrates the relative levels of anti-WSG IgA at day 21 (panel 3A) and day 101 (panel 3B) in the saliva of rats immunized with the GTF-WSG conjugate as compared to GTF or WSG alone, or PBS (sham).
Figure 3B:
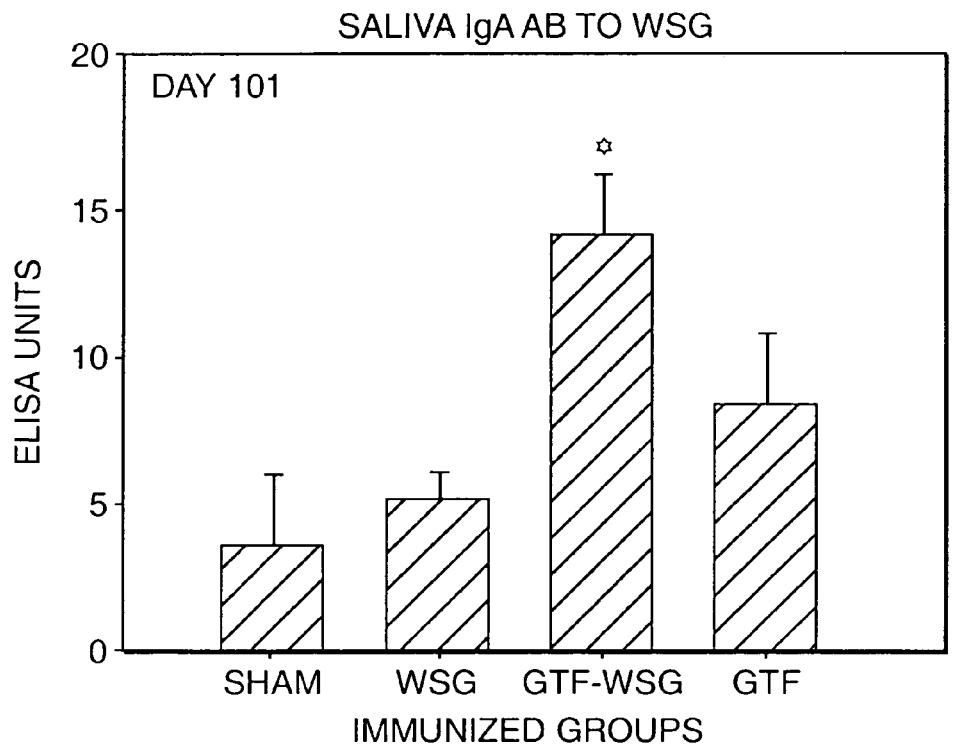
Figure 4A:
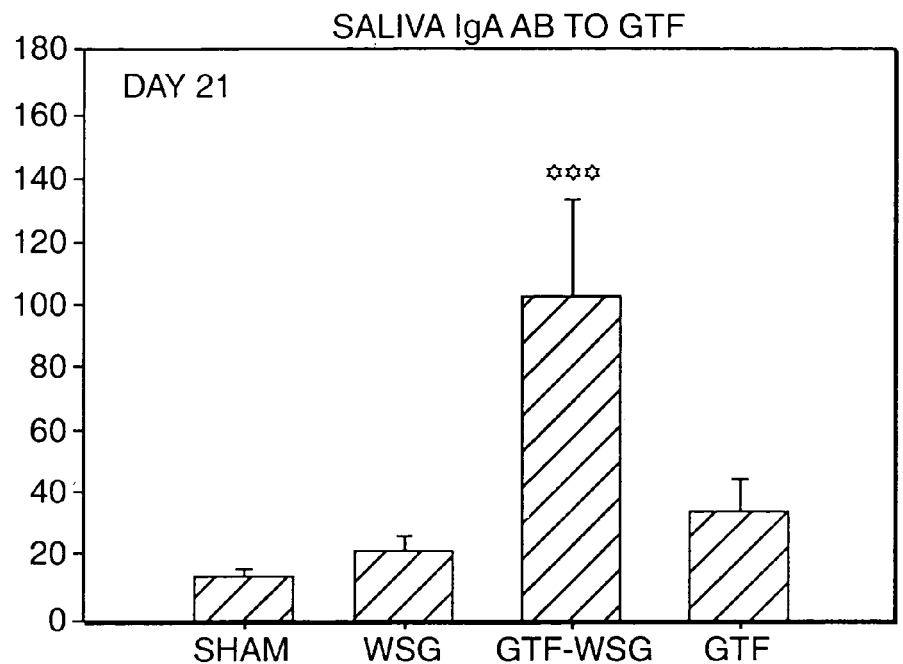
FIGS. 4A–4C illustrates the relative levels of salivary anti-GTF IgA 21, 35, and 101 days after primary inoculation (panels 4A, 4B, and 4C, respectively) with PBS (sham), WSG, GTF-WSG, or GTF.
Figure 4B:
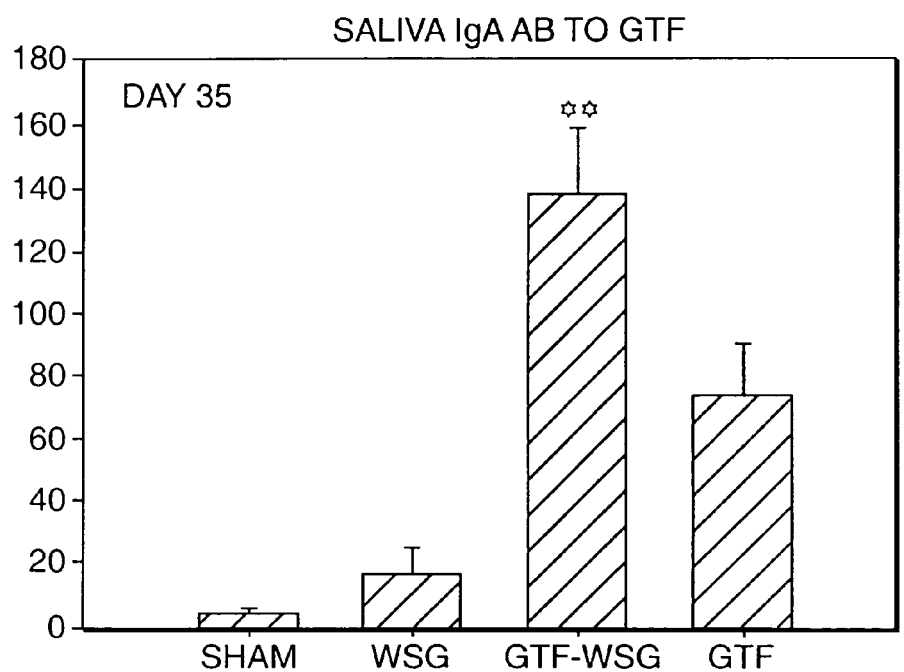
Figure 4C:
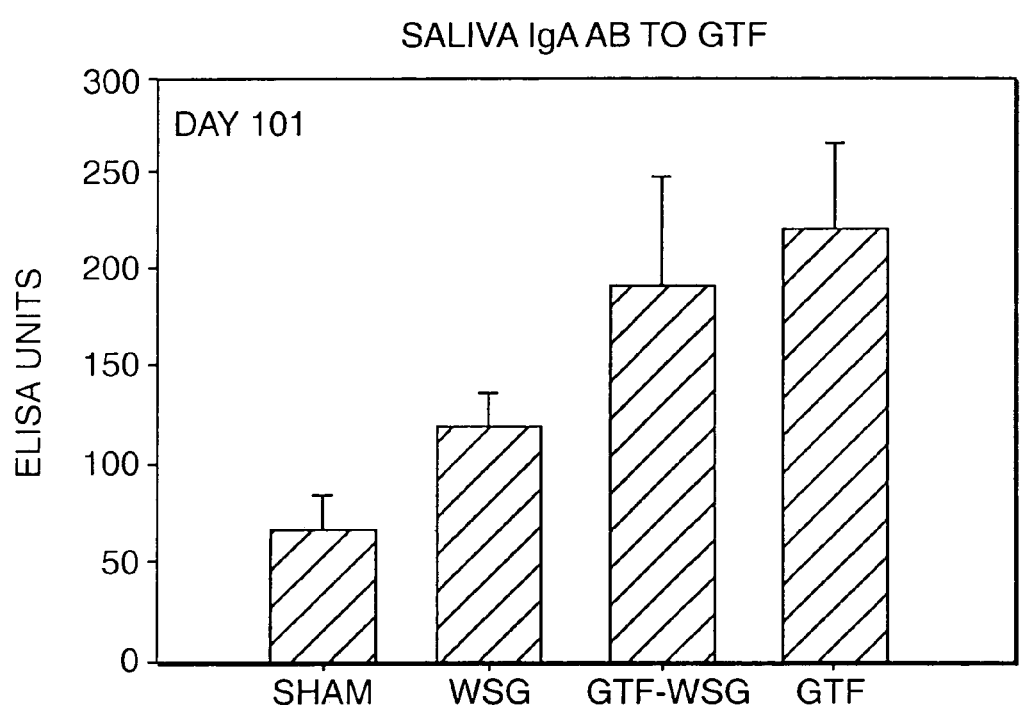

Blood and saliva samples taken on d14, d21, d35, d47, and d101 were analyzed for levels of serum IgG and salivary IgA antibodies against WSG and GTF. Higher levels of salivary anti-WSG IgA were induced by the conjugate than by GTF alone (FIG. 3A). These levels remained elevated through d101 (FIG. 3B). Similarly, salivary IgA antibodies directed against GTF were substantially elevated after GTF-WSG immunization (FIGS. 4A–C).

EXAMPLE 6

Glucan Conjugate Vaccines Reduce the Incidence of Dental Caries

The sacrificed animals of Example 5 are examined for caries. The extent and depth of carious lesions in all rat molar teeth are evaluated microscopically using the modified Keyes method described in Taubman and Smith, J. Immunol. 118:710–20 (1977), incorporated by reference. Caries scores are determined separately on smooth and occlusal surfaces.

Comparison of caries scores between controls and animals vaccinated with the compositions of the invention will demonstrate that the claimed compositions elicit protection against dental caries.

EXAMPLE 7

Peptide and Multi-Peptide Conjugate Vaccines

Immunogenic conjugates comprising a TD carrier protein and any number of peptide moieties can be prepared as follows. The TD-peptide conjugates can be used in a vaccine formulation or be used to prepare a dual conjugate composition with a T cell-independent antigen such as a dextran or glucan, preferably a water soluble glucan.

The following peptides were synthesized:

Peptide STGLU: CAGA-TGAQTIKGQKLYFKANGQQVKG   (SEQ ID NO: 43)

Peptide HDS:   CAGA-VPSYSFIRAHDSEVQDLIA      (SEQ ID NO: 44)

Peptide CAT:   DANFDSIRVDAVDNVDADLLQ         (SEQ ID NO: 38)

Peptides STGLU and HDS correspond to SEQ ID NOS:7 and 27 with the addition of the four amino acid spacer, CAGA, to the amino end. The amino terminal cysteine of this linker on STGLU and HDS are useful in coupling reactions. Peptide CAT corresponds to SEQ ID NO:39. For the purpose the coupling reaction, peptide CAT was synthesized with an N terminal amine and no lysine residues.

Tetanus Toxoid Bromacetylation

Tetanus toxoid (TT) was bromacetylated as follows: 8 mg of TT, (obtained from SmithKline Beecham, Rixensart, Belgium) was solubilized in 0.54 ml of 2 M NaCl. 100 μl of HE buffer added to the solubilized TT. (HE buffer=0.15 M HEPES, 2 mM EDTA, pH 7.3). 3 mg of N-hydroxysuccinimidyl bromoacetate (BioAffinity Systems, Roscoe, Ill.) in 127 μl of dimethylformamide (DMF) was added to the solution while vortexing. After 2 hr at room temp in the dark, 2 M NaCl was added to a final volume of 4 ml. Unreacted reagent removed by ultrafiltration in an Ultrafree 30 device (Millipore Corp.). The final volume was about 0.56 ml.

CAT Thiolation

In a separate reaction, the N-terminal amine of peptide CAT was thiolated as follows: 5 mg of the peptide was solubilized in 0.5 ml HE buffer and 25 μl of N-hydroxysuccinimidyl dithiopyridyl proptionate (SPDP, BioAffinity Systems) (0.1 M in DMF) added. After a 1 hr incubation, 1 mg of dithiothreitol (DTT) was added. The peptide was than desalted on a 1×55 cm G-10 column (Pharmacia), equilibrated with 10 mM sodium acetate, 0.15 M NaCl, 2 mM EDTA, pH 5 (NaAc buffer).

HDS and STGLU Preparation 11 mg of peptide was solubized in 1 ml HE buffer and 28 mg of DTT added. 10.5 mg of peptide was solubilized in 0.5 ml HE buffer and 25 mg of DTT added. After about 2 hr, peptides HDS and STGLU were desalted as described above.

The thiol content of each peptide solution was determined using dithionitrobenzene (Ellman's reagent) and were found to be 115 μM (CAT), 154 μM (HDS), and 370 μM (STGLU).

Conjugation

Four conjugates were prepared using the above bromoacetylated TT and one or more thiolated peptides beginning with the following solutions. Pair-wise combinations of thiolated peptides may also be conjugated to the TT.

(TTA)    1.25 ml CAT + 60 μl TT +
             50 μl 1 M HEPES, pH 8.

(TTB)    2.5 ml HDS, 160 μl TT +
             100 μl 1 M HEPES, pH 8.

(TTC)    2.4 ml STGLU + 160 μl TT +
             50 μl 1 M HEPES, pH 8.

(TTABC)  1.25 ml CAT + 1.4 ml HDS + 1.2 ml STGLU +
             180 μl TT + 100 μl 1 M HEPES, pH 8.

Each of the above solutions was saturated with nitrogen to deoxygenate and coupling reactions were allowed to proceed overnight at 4° C. The pH was then readjusted to 8 with 1 N NaOH and the solutions were incubated overnight at 4° C. The reaction was then quenched by the addition of 50 μl of 50 mM 2-mercaptoethanol.

Unconjugated peptide was removed from each reaction by gel filtration on a 1×60 cm S200HR column (Pharmacia), equilibrated with PBS. The fractions containing the TT were pooled, and the total protein content determined using the MicroBCA assay (BioRad), with TT as the standard. The protein concentration of each conjugate is recited in Table III.

TABLE III

| TT-Conjugate | Constituent Peptides | Protein Concentration |
|---|---|---|
| TTA | CAT | 130 µg/ml |
| TTB | HDS | 290 µg/ml |
| TTC | STGLU | 260 µg/ml |
| TTABC | CAT, HDS, STGLU | 290 µg/ml |

Conjugates were then sterile filtered using a Millex GV 0.2µ filter (Millipore) in preparation for administration to a patient. The above conjugates may also be further conjugated to a T cell independent antigen, polysaccharide, dextran, or glucan, with or without a linker, essentially as described for the conjugation of tetanus toxoid in Example I. For conjugation, it is preferred that the TT-peptide conjugates are concentrated to about 10–20 mg/ml using standard techniques, such as centrifugal concentration using, for example, a MILLIPORE Centricon-10 microconcentrator.

CDAP Conjugation of TT-Peptide Conjugates to WSG (TTA-WSG, TTB-WSG, TTC-WSG, and TTABC-WSG)

WSG is suspended in water @ 10 mg/ml on ice, CDAP @ 100 mg/ml in acetonitrile. At time zero, 18 µl of CDAP solution is slowly added, with stirring, to 0.25 ml of the WSG glucan solution at RT. At 30 seconds, the pH is raised with 18 µl of 0.2 M TEA (triethylamine). At 60 seconds, an additional 9 µl of TEA is added. At 2.5 minutes, a solution of 150 µl of TTA, TTB, TTC, or TTABC and 25 µl of 100 mM sodium borate, pH 9.3, are added with stirring. The coupling reaction is allowed to proceed for 30 minutes at RT, and then quenched by addition of 100 µl of 1M glycine, pH 9.3. TT-peptide molecules unconjugated to the WSG are removed by gel filtration on a 1×60 cm S400HR column (Pharmacia), equilibrated in PBS. The void volume fractions containing the TT-peptide-WSG conjugate are pooled and sterile filtered with an 0.2 µm Millipore GV filter. Protein concentration in the pool are determined using the Coomassie Plus assay (Pierce Chemical). The concentration of polysaccharides are determined using the resorcinol assay of Monsigny et al., Anal. Chem., Vol. 175, p. 525 (1988) and the protein/carbohydrate ratio of the TT-peptide-WSG conjugates are calculated.

Administration of TT-Peptide-WSG Conjugates to a Patient

Groups of mutans-free male Sprague-Dawley rats of approximately 40 days of age were injected subcutaneously in the vicinity of the salivary glands on d0 with PBS, or 10 µg doses of TTA-WSG, TTB-WSG, TTC-WSG, or TTABC-WSG, as described above, each emulsified in Freund's complete adjuvant. On d7, each animal was boosted with the same dose of antigen or PBS in incomplete Freund's adjuvant (IFA).

Beginning on day 22, rats were orally infected with approximately $10^8$ S. sobrinus 6715 cells for 3 consecutive days. Rats were terminated at approximately d101 and prepared for caries examination.

The extent and depth of carious lesions in all rat molar teeth are evaluated microscopically using the modified Keyes method described in Taubman and Smith, J. Immunol. 118:710–20 (1977). Comparison of scores between controls and animals vaccinated with the compositions of the invention will show a reduced incidence and severity of caries in the vaccinated animals.

EXAMPLE 8

Glucan Conjugate Vaccine Elicits Anti-GTF and Anti-Glucan Antibodies

Groups of Sprague-Dawley rats free of indigenous mutans streptococci were weaned at approximately 20 days and raised on high sucrose Diet 2000. At approximately 28 days, rats immunized either intranasally (in) or subcutaneously (sc) in the salivary gland vicinity with 10 µg doses of the GTF-WSG conjugate preparation of Example 1. 11 sham-immunized rats served as controls: 6 rats were injected on day 0 with PBS and complete Freund's adjuvant and 5 rats were intranasally inoculated with PBS using Cholera toxin (ct) as an adjuvant. The sham immunizations were repeated on day 7 using incomplete Freund's (sc) and CT (in).

A total of 27 rats were immunized with the GTF-WSG conjugate on the same schedule. 6 rats were injected with the conjugate in Freund's complete (day 0) and incomplete (day 7) adjuvant. 21 rats were intranasally inoculated with the conjugate on day 0, either with (n=15) or without (n=6) cholera toxin adjuvant. Secondary inoculations were given on day 7 in 15 animals with CT and 6 without adjuvant.

Serum and saliva samples were obtained from all animals on day 21 indicated that treatment with the GTF-WSG conjugate elicited anti-GTF and anti-WSG antibodies by day 21. Also on day 21, the animals were infected with S. sobrinus 6715 cells for 3 consecutive days as described in Example 5. The infection was allowed to proceed for 78 days at which time the animals were euthanized and prepared for caries examination.

Effect of Administration Route on Antibody Titer and Isotype Ratio

Serum and saliva samples obtained on day 21 were analyzed by ELISA essentially as described in Example 3 and compiled in the following tables.

TABLE IV

Antibody to GTF in serum and saliva
(means ± std error)

| | Total Serum IgG (EU × 100) | Serum IgM (ng/ml) | Serum IgA (EU) |
|---|---|---|---|
| sham | 21 ± 7 | 288 ± 490 | 26 ± 6 |
| GTF-WSG/CT/in | 322 ± 108 | 13858 ± 1062 | 2502 ± 423 |
| GTF-WSG/CFA/sc | 3977 ± 744 | 54149 ± 15037 | 1811 ± 727 |
| GTF-WSG/in | 30 ± 18 | 6055 ± 2412 | 549 ± 194 |

Total serum IgG reactive with GTF was substantially elevated in animals vaccinated in or sc with adjuvant. Serum IgM and salivary IgA levels reactive with GTF were significantly enhanced in all groups exposed to the vaccine, but was substantially higher where the antigen was given with adjuvant. Among these animals, serum IgM was greatest in the injected animals, whereas salivary IgA was highest in the intranasally inoculated group.

TABLE V

Antibody to WSG in serum and saliva
(means ± std error)

|  | Total Serum IgG (EU) | Serum IgM (ng/ml) | Serum IgA (EU) |
| --- | --- | --- | --- |
| sham | 772 ± 95 | 947 ± 257 | 71 ± 22 |
| GTF-WSG/CT/in | 4838 ± 511 | 7446 ± 634 | 1758 ± 448 |
| GTF-WSG/CFA/sc | 6683 ± 904 | 23446 ± 6353 | 694 ± 503 |
| GTF-WSG/in | 1600 ± 505 | 1424 ± 315 | 1414 ± 674 |

Total serum IgG was elevated in all animals exposed to the conjugate. Anti-WSG serum IgM levels were markedly highest in the injected animals. Levels of WSG-specific IgA in salivary samples were highest in intranasally inoculated animals, whether or not the conjugate was administered with Cholera toxin.

Interestingly, the mean ratio of IgG1/IgG2a in sc-injected animals was 0.4:1 for anti-WSG antibodies and 4.5:1 for anti-GTF antibodies. In contrast, the mean ratio of IgG1/IgG2a of intranasally inoculated animals was 0.6:1 for anti-WSG antibodies and 1.9:1 for anti-GTF antibodies, indicating that isotype ratios be manipulated by varying the route of immunization.

EXAMPLE 9

Antibodies Raised Against GTF-WSG Inhibit WSG and WIG Synthesis In Vitro

Serum antibodies from the WSG-treated animals of Example 8 were assayed for the ability to inhibit GTF-mediated incorporation of glucose into WSG or WIG. As expected, sera from immunized animals was substantially more effective at inhibiting GTF activity. Surprisingly, however, subcutaneous immunization resulted in greater inhibition of WIG synthesis by GTF as compared to sera from the intranasally inoculated animals. Conversely, sera from the intranasal group showed elevated inhibition of WSG synthesis as compared to the subcutaneously inoculated animals.

These studies show that isotype ratios be manipulated by varying the route of immunization, moreover, the different isotypes differentially inhibit the GTF function. Varying the isotype balance thus permits the targeted interruptions of different points in the GTF-glucan virulence pathway.

EXAMPLE 10

Glucan Conjugate Vaccine Reduces the Incidence of Dental Caries

Animals from the control and adjuvant-treated vaccine groups were from Example 7 were evaluated for dental caries. The extent and depth of carious lesions on the smooth and occlusal surfaces of all rat molar teeth were then evaluated microscopically using the modified Keyes method described in Taubman and Smith, J. Immunol. 118:710–20 (1977). As illustrated by the data in Table VI, vaccination with the GTF-WSG conjugate reduced the incidence of dental caries by over 50%.

TABLE VI

Conjugate Vaccine Reduces Incidence of Dental Caries by More Than 50%

| Treatment | Mean Caries score | std error |
| --- | --- | --- |
| Sham (n = 11) | 60.7 | ±4.1 |
| GTF-WSG CT/in (n = 15) | 26.6 | ±2.3 |

---

The invention claimed is:

1. An immunogenic composition comprising a purified cariogenic mutans streptococcal glucan and an isolated cariogenic mutans streptococcal glucosyltransferase (GTF), a recombinant fusion protein of said GTF, or an immunogenic peptide of said GTF, wherein the cariogenic mutans streptococcal GTF, the recombinant fusion protein of said GTF, or the immunogenic peptide of said GTF is covalently conjugated to the cariogenic mutans streptococcal glucan by an isourea bond formed by 1-cyano-4-dimethylamino-pyridinium-tetrafluoroborate (CDAP) activation, and wherein the immunogenic composition elicits antibodies to both the cariogenic mutans streptococcal glucan and the cariogenic mutans streptococcal GTF, the recombinant fusion protein of said GTF, or the immunogenic peptide of said GTF.

2. An immunogenic composition comprising a purified cariogenic mutans streptococcal glucan and an isolated cariogenic mutans streptococcal protein selected from the group consisting of glucosyltransferase (GTF), a recombinant fusion protein of said GTF, an AgI/II adhesion protein, a glucan binding protein (GBP), and an immunogenic peptide of said GTF, GBP or AgI/II adhesion protein, wherein the cariogenic mutans streptococcal protein is covalently conjugated to the cariogenic mutans streptococcal glucan by an isourea bond formed by 1-cyano-4-dimethylamino-pyridinium-tetrafluoroborate (CDAP) activation, and wherein the immunogenic composition elicits antibodies to both the cariogenic mutans streptococcal glucan and the cariogenic mutans streptococcal protein.

3. The immunogenic composition of claim 2, wherein the cariogenic mutans streptococcal glucan is water-soluble glucan (WSG).

4. The immunogenic composition of claim 2, wherein the cariogenic mutans streptococcal glucan is from *S. mutans*.

5. The immunogenic composition of claim 2, wherein the cariogenic mutans streptococcal glucan is from *S. sobrinus*.

6. The immunogenic composition of claim 2, wherein the mutans streptococcal protein induces antibodies that specifically bind to an epitope of a cariogenic mutans *streptococcus*.

7. The immunogenic composition of claim 2, wherein the antibodies inhibit the catalytic or glucan-binding activity of said GTF.

8. The immunogenic composition of claim 2, wherein the antibodies inhibit the binding activity of said GBP.

9. The immunogenic composition of claim 2, wherein the antibodies inhibit the binding activity of said AgI/II adhesion protein.

10. The immunogenic composition of claim 2, further comprising an additional moiety conjugated to the cariogenic mutans streptococcal glucan and/or to the cariogenic mutans streptococcal protein, wherein the additional moiety is selected from a hapten, protein, peptide, detoxified lipopolysaccharide, carbohydrate, or lipid.

11. The immunogenic composition of claim 2, wherein the cariogenic mutans streptococcal glucan is covalently conjugated to the cariogenic mutans streptococcal protein through a spacer, linker, amino acid, peptide, protein, or hapten.

12. An immunogenic composition comprising a purified cariogenic mutans streptococcal glucan and an isolated cariogenic mutans streptococcal protein selected from the group consisting of glucosyltransferase (GTF), a recombinant fusion protein of said GTF, and an immunogenic peptide of said GTF, wherein the cariogenic mutans streptococcal protein is covalently conjugated to the cariogenic streptococcal glucan by an isourea bond formed by 1-cyano-4-dimethylamino-pyridinium-tetrafluoroborate (CDAP) activation, and wherein the immunogenic composition induces IgA and IgG antibodies that specifically bind to a cariogenic mutans streptococcal protein and IgA and IgG antibodies that specifically bind to a cariogenic mutans streptococcal glucan.

13. The immunogenic composition of claim 12, wherein the streptococcal glucan is from *S. mutans*.

14. The immunogenic composition of claim 12, wherein the streptococcal glucan is from *S. sobrinus*.

15. The immunogenic composition of claim 12, wherein the streptococcal glucan comprises at least one of $\alpha$-1,3 or $\alpha$-1,6 glucoside linkage.

16. The immunogenic composition of claim 12, further comprising an additional moiety conjugated to the streptococcal glucan and/or to the cariogenic mutans streptococcal protein, wherein the additional moiety is selected from a hapten, protein, peptide, detoxified lipopolysaccharide, carbohydrate, or lipid.

17. The immunogenic composition of claim 12, wherein the mutans streptococcal protein induces antibodies that specifically bind to an epitope of a cariogenic mutans *streptococcus*.

18. The immunogenic composition of claim 12, wherein the streptococcal glucan is covalently conjugated to the cariogenic mutans streptococcal protein through a spacer, linker, amino acid, peptide, protein, or hapten.

* * * * *

SEQUENCE LISTING

<160> NUMBER OF SEQ ID NOS: 44

<210> SEQ ID NO 1
<211> LENGTH: 15
<212> TYPE: PRT
<213> ORGANISM: Streptococcus sp.

<400> SEQUENCE: 1

Gly Ala Val Asp Ser Ile Leu Gly Gly Val Ala Thr Tyr Gly Ala
 1               5                  10                  15

<210> SEQ ID NO 2
<211> LENGTH: 15
<212> TYPE: PRT
<213> ORGANISM: Streptococcus sp.

<400> SEQUENCE: 2

Tyr Glu Lys Glu Pro Thr Thr Pro Pro Thr Arg Thr Pro Asp Gln
 1               5                  10                  15

<210> SEQ ID NO 3
<211> LENGTH: 16
<212> TYPE: PRT
<213> ORGANISM: Streptococcus sp.

<400> SEQUENCE: 3

Thr Pro Glu Asp Pro Thr Asp Pro Thr Asp Pro Gln Asp Pro Ser Ser
 1               5                  10                  15

<210> SEQ ID NO 4
<211> LENGTH: 20
<212> TYPE: PRT
<213> ORGANISM: Streptococcus sp.

<400> SEQUENCE: 4

Ala Asn Ala Ala Asn Glu Ala Asp Tyr Gln Ala Lys Leu Thr Ala Tyr
 1               5                  10                  15

Gln Thr Glu Cys
            20

<210> SEQ ID NO 5
<211> LENGTH: 20
<212> TYPE: PRT
<213> ORGANISM: Streptococcus sp.

<400> SEQUENCE: 5

Asp Gly Lys Leu Arg Tyr Tyr Asp Ala Asn Ser Gly Asp Gln Ala Phe
 1               5                  10                  15

Asn Lys Ser Val
            20

<210> SEQ ID NO 6
<211> LENGTH: 25
<212> TYPE: PRT
<213> ORGANISM: Streptococcus sp.

<400> SEQUENCE: 6

Pro Leu Asp Lys Arg Ser Gly Leu Asn Pro Leu Ile His Asn Ser Leu
 1               5                  10                  15

Val Asp Arg Glu Val Asp Asp Arg Glu
            20                  25

<210> SEQ ID NO 7
<211> LENGTH: 22
<212> TYPE: PRT
<213> ORGANISM: Streptococcus sp.

<400> SEQUENCE: 7

Thr Gly Ala Gln Thr Ile Lys Gly Gln Lys Leu Tyr Phe Lys Ala Asn
 1               5                  10                  15

Gly Gln Gln Val Lys Gly
            20

<210> SEQ ID NO 8
<211> LENGTH: 14
<212> TYPE: PRT
<213> ORGANISM: Streptococcus sp.

<400> SEQUENCE: 8

Gln Trp Asn Gly Glu Ser Glu Lys Pro Tyr Asp Asp His Leu
 1               5                  10

```
<210> SEQ ID NO 9
<211> LENGTH: 19
<212> TYPE: PRT
<213> ORGANISM: Streptococcus sp.

<400> SEQUENCE: 9

Gly Gly Tyr Glu Phe Leu Leu Ala Asn Asp Val Asp Asn Ser Asn Pro
 1               5                  10                  15

Val Val Gln

<210> SEQ ID NO 10
<211> LENGTH: 19
<212> TYPE: PRT
<213> ORGANISM: Streptococcus sp.

<400> SEQUENCE: 10

Ala Asn Asp Val Asp Asn Ser Asn Pro Val Val Gln Ala Glu Gln Leu
 1               5                  10                  15

Asn Trp Leu

<210> SEQ ID NO 11
<211> LENGTH: 26
<212> TYPE: PRT
<213> ORGANISM: Streptococcus sp.

<400> SEQUENCE: 11

Gly Gly Tyr Glu Phe Leu Leu Ala Asn Asp Val Asp Asn Ser Asn Pro
 1               5                  10                  15

Val Val Gln Ala Glu Gln Leu Asn Trp Leu
            20                  25

<210> SEQ ID NO 12
<211> LENGTH: 26
<212> TYPE: PRT
<213> ORGANISM: Streptococcus sp.

<400> SEQUENCE: 12

Gly Gly Tyr Glu Asp Leu Leu Ala Asn Asp Val Asp Asn Ser Asn Pro
 1               5                  10                  15

Val Val Gln Ala Glu Gln Leu Asn Trp Leu
            20                  25

<210> SEQ ID NO 13
<211> LENGTH: 26
<212> TYPE: PRT
<213> ORGANISM: Streptococcus sp.

<400> SEQUENCE: 13

Gly Gly Tyr Glu Phe Leu Leu Ala Asn Asp Val Asp Asn Ser Asn Pro
 1               5                  10                  15

Ile Val Gln Ala Glu Gln Leu Asn Trp Leu
            20                  25

<210> SEQ ID NO 14
<211> LENGTH: 26
<212> TYPE: PRT
<213> ORGANISM: Streptococcus sp.

<400> SEQUENCE: 14

Ala Gly Tyr Glu Leu Leu Leu Ala Asn Asp Val Asp Asn Ser Asn Pro
 1               5                  10                  15

Val Val Gln Ala Glu Gln Leu Asn His Leu
```

20          25

<210> SEQ ID NO 15
<211> LENGTH: 23
<212> TYPE: PRT
<213> ORGANISM: Streptococcus sp.

<400> SEQUENCE: 15

Asp Ala Asn Phe Asp Ser Ile Arg Val Asp Ala Val Asp Asn Val Asp
 1               5                  10                  15

Ala Asp Val Val Gln Ile Ala
            20

<210> SEQ ID NO 16
<211> LENGTH: 23
<212> TYPE: PRT
<213> ORGANISM: Streptococcus sp.

<400> SEQUENCE: 16

Asp Ala Asn Phe Asp Ser Ile Arg Val Asp Ala Glu Asp Asn Val Asp
 1               5                  10                  15

Ala Asp Gln Leu Gln Ile Ser
            20

<210> SEQ ID NO 17
<211> LENGTH: 9
<212> TYPE: PRT
<213> ORGANISM: Streptococcus sp.

<400> SEQUENCE: 17

Asp Ser Ile Arg Val Asp Ala Val Asp
 1               5

<210> SEQ ID NO 18
<211> LENGTH: 14
<212> TYPE: PRT
<213> ORGANISM: Streptococcus sp.

<400> SEQUENCE: 18

Tyr Glu Lys Glu Pro Thr Pro Pro Thr Arg Thr Pro Asp Gln
 1               5                  10

<210> SEQ ID NO 19
<211> LENGTH: 15
<212> TYPE: PRT
<213> ORGANISM: Streptococcus sp.

<400> SEQUENCE: 19

Ser Ala Trp Asn Ser Asp Ser Glu Lys Pro Phe Asp Asp His Leu
 1               5                  10                  15

<210> SEQ ID NO 20
<211> LENGTH: 21
<212> TYPE: PRT
<213> ORGANISM: Streptococcus sp.

<400> SEQUENCE: 20

Ala Asn Asp His Leu Ser Ile Leu Glu Ala Trp Ser Asp Asn Asp Thr
 1               5                  10                  15

Pro Tyr Leu His Asp
            20

<210> SEQ ID NO 21

```
<211> LENGTH: 21
<212> TYPE: PRT
<213> ORGANISM: Streptococcus sp.

<400> SEQUENCE: 21

Ala Asn Asp His Leu Ser Ile Leu Glu Ala Trp Ser Tyr Asn Asp Thr
 1               5                  10                  15
Pro Tyr Leu His Asp
            20

<210> SEQ ID NO 22
<211> LENGTH: 21
<212> TYPE: PRT
<213> ORGANISM: Streptococcus sp.

<400> SEQUENCE: 22

Ala Ile Asn His Leu Ser Ile Leu Glu Ala Trp Ser Asp Asn Asp Pro
 1               5                  10                  15
Gln Tyr Asn Lys Asp
            20

<210> SEQ ID NO 23
<211> LENGTH: 21
<212> TYPE: PRT
<213> ORGANISM: Streptococcus sp.

<400> SEQUENCE: 23

Ala Asn Asn His Val Ser Ile Val Glu Ala Trp Ser Asp Asn Asp Thr
 1               5                  10                  15
Pro Tyr Leu His Asp
            20

<210> SEQ ID NO 24
<211> LENGTH: 21
<212> TYPE: PRT
<213> ORGANISM: Streptococcus sp.

<400> SEQUENCE: 24

Ala Ile Asp His Leu Ser Ile Leu Glu Ala Trp Ser Gly Asn Asp Asn
 1               5                  10                  15
Asp Tyr Val Lys Gln
            20

<210> SEQ ID NO 25
<211> LENGTH: 21
<212> TYPE: PRT
<213> ORGANISM: Streptococcus sp.

<400> SEQUENCE: 25

Ala Asn Asn His Val Ser Ile Val Glu Ala Trp Ser Asp Asn Asp Thr
 1               5                  10                  15
Pro Tyr Leu His Asp
            20

<210> SEQ ID NO 26
<211> LENGTH: 20
<212> TYPE: PRT
<213> ORGANISM: Streptococcus sp.

<400> SEQUENCE: 26

Val Pro Ser Tyr Ser Phe Ile Arg Thr Ala His Asp Ser Glu Val Gln
 1               5                  10                  15
```

-continued

Asp Leu Ile Ala
          20

<210> SEQ ID NO 27
<211> LENGTH: 19
<212> TYPE: PRT
<213> ORGANISM: Streptococcus sp.

<400> SEQUENCE: 27

Val Pro Ser Tyr Ser Phe Ile Arg Ala His Asp Ser Glu Val Gln Asp
 1               5                  10                  15

Leu Ile Ala

<210> SEQ ID NO 28
<211> LENGTH: 22
<212> TYPE: PRT
<213> ORGANISM: Streptococcus sp.

<400> SEQUENCE: 28

Val Pro Ser Tyr Ser Phe Ile Arg Ala His Asp Ser Glu Val Gln Asp
 1               5                  10                  15

Leu Ile Arg Asn Ile Ile
          20

<210> SEQ ID NO 29
<211> LENGTH: 22
<212> TYPE: PRT
<213> ORGANISM: Streptococcus sp.

<400> SEQUENCE: 29

Met Ala Asn Tyr Ile Phe Ile Arg Ala His Asp Ser Glu Val Gln Thr
 1               5                  10                  15

Val Ile Ala Lys Ile Ile
          20

<210> SEQ ID NO 30
<211> LENGTH: 22
<212> TYPE: PRT
<213> ORGANISM: Streptococcus sp.

<400> SEQUENCE: 30

Val Pro Ser Tyr Ser Phe Ala Arg Ala His Asp Ser Glu Val Gln Asp
 1               5                  10                  15

Leu Ile Arg Asp Ile Ile
          20

<210> SEQ ID NO 31
<211> LENGTH: 22
<212> TYPE: PRT
<213> ORGANISM: Streptococcus sp.

<400> SEQUENCE: 31

Val Pro Asn Tyr Val Phe Ile Arg Ala His Asp Ser Glu Val Gln Thr
 1               5                  10                  15

Arg Ile Ala Lys Ile Ile
          20

<210> SEQ ID NO 32
<211> LENGTH: 22
<212> TYPE: PRT
<213> ORGANISM: Streptococcus sp.

<400> SEQUENCE: 32

```
Val Pro Ser Tyr Ser Phe Ala Arg Ala His Asp Ser Glu Val Gln Asp
  1               5                  10                  15

Ile Ile Arg Asp Ile Ile
                20
```

<210> SEQ ID NO 33
<211> LENGTH: 15
<212> TYPE: PRT
<213> ORGANISM: Streptococcus sp.

<400> SEQUENCE: 33

```
Pro Gln Trp Asn Gly Glu Ser Glu Lys Pro Tyr Asp Asp His Leu
  1               5                  10                  15
```

<210> SEQ ID NO 34
<211> LENGTH: 15
<212> TYPE: PRT
<213> ORGANISM: Streptococcus sp.

<400> SEQUENCE: 34

```
Ser Ala Trp Asn Ser Asp Ser Glu Lys Pro Phe Asp Asp His Leu
  1               5                  10                  15
```

<210> SEQ ID NO 35
<211> LENGTH: 15
<212> TYPE: PRT
<213> ORGANISM: Streptococcus sp.

<400> SEQUENCE: 35

```
Pro Asn Trp Asn Ser Gln Thr Glu Ser Asp Thr Ser Ala Gly Glu
  1               5                  10                  15
```

<210> SEQ ID NO 36
<211> LENGTH: 15
<212> TYPE: PRT
<213> ORGANISM: Streptococcus sp.

<400> SEQUENCE: 36

```
Pro Gln Trp Asn Gly Glu Ser Glu Lys Pro Tyr Asp Asp His Leu
  1               5                  10                  15
```

<210> SEQ ID NO 37
<211> LENGTH: 22
<212> TYPE: PRT
<213> ORGANISM: Streptococcus sp.

<400> SEQUENCE: 37

```
Thr Gly Ala Arg Thr Ile Asn Gly Gln Leu Leu Tyr Phe Arg Ala Asn
  1               5                  10                  15

Gly Val Gln Val Lys Gly
                20
```

<210> SEQ ID NO 38
<211> LENGTH: 21
<212> TYPE: PRT
<213> ORGANISM: Streptococcus sp.

<400> SEQUENCE: 38

```
Asp Ala Asn Phe Asp Ser Ile Arg Val Asp Ala Val Asp Asn Val Asp
  1               5                  10                  15

Ala Asp Leu Leu Gln
                20
```

<210> SEQ ID NO 39
<211> LENGTH: 19
<212> TYPE: PRT
<213> ORGANISM: Streptococcus sp.

<400> SEQUENCE: 39

Asp Gly Gln Val Gln Tyr Phe Asp Glu Met Gly Tyr Gln Ala Lys Gly
 1               5                  10                  15

Lys Phe Val

<210> SEQ ID NO 40
<211> LENGTH: 19
<212> TYPE: PRT
<213> ORGANISM: Streptococcus sp.

<400> SEQUENCE: 40

Pro Asn Lys Tyr Gly Thr Ala Asp Asp Leu Val Lys Ala Ile Lys Ala
 1               5                  10                  15

Leu His Ser

<210> SEQ ID NO 41
<211> LENGTH: 19
<212> TYPE: PRT
<213> ORGANISM: Streptococcus sp.

<400> SEQUENCE: 41

Leu Val Lys Ala Ile Lys Ala Leu His Ser Lys Gly Ile Lys Val Met
 1               5                  10                  15

Ala Asp Trp

<210> SEQ ID NO 42
<211> LENGTH: 19
<212> TYPE: PRT
<213> ORGANISM: Streptococcus sp.

<400> SEQUENCE: 42

Val Met Ala Asp Trp Val Pro Asp Gln Met Tyr Ala Phe Pro Glu Lys
 1               5                  10                  15

Glu Val Val

<210> SEQ ID NO 43
<211> LENGTH: 26
<212> TYPE: PRT
<213> ORGANISM: Streptococcus sp.

<400> SEQUENCE: 43

Cys Ala Gly Ala Thr Gly Ala Gln Thr Ile Lys Gly Gln Lys Leu Tyr
 1               5                  10                  15

Phe Lys Ala Asn Gly Gln Gln Val Lys Gly
                20                  25

<210> SEQ ID NO 44
<211> LENGTH: 23
<212> TYPE: PRT
<213> ORGANISM: Streptococcus sp.

<400> SEQUENCE: 44

Cys Ala Gly Ala Val Pro Ser Tyr Ser Phe Ile Arg Ala His Asp Ser
 1               5                  10                  15

Glu Val Gln Asp Leu Ile Ala